(12) United States Patent
Zuker et al.

(10) Patent No.: US 7,407,769 B2
(45) Date of Patent: Aug. 5, 2008

(54) METHOD OF IDENTIFYING ACTIVITY MODULATORS OF A POLYCYSTIN-2L1 TASTE RECEPTOR POLYPEPTIDE

(75) Inventors: Charles Zuker, Del Mar, CA (US); Angela L. Huang, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 216 days.

(21) Appl. No.: 11/176,958

(22) Filed: Jul. 6, 2005

(65) Prior Publication Data

US 2007/0009912 A1   Jan. 11, 2007

(51) Int. Cl.
*G01N 33/567* (2006.01)
*G01N 33/53* (2006.01)
*C07K 14/00* (2006.01)

(52) U.S. Cl. .................. 435/7.2; 435/7.21; 435/7.1; 530/350

(58) Field of Classification Search .................. None
See application file for complete search history.

(56) References Cited

U.S. PATENT DOCUMENTS

| 2002/0037515 A1 | 3/2002 | Margolskee et al. |
| 2002/0127623 A1* | 9/2002 | Minshull et al. ........... 435/7.92 |

FOREIGN PATENT DOCUMENTS

| WO | WO 00/44929 A2 | 8/2000 |
| WO | WO 00/45179 * | 8/2000 |
| WO | WO 00/45179 A2 | 8/2000 |
| WO | WO 03/025137 * | 3/2003 |

OTHER PUBLICATIONS

Chen et al., Polycystin-L is a calcium regulated cation channel permeable to calcium ions. Nature, 401, 383-385, 1999.*
Alexander et al. (1992) "Altering the antigenicity of proteins" *Proc. Natl. Acad. Sci. USA* 89: 3352-3356.
Avenet & Lindemann (1989) "Perspectives in taste reception" *J Membr Biol.*112, 1-8.
Basora et al. (2002) "Tissue and Cellular Localization of a Novel Polycystic Kidney Disease-Like Gene Product, Polycystin-L" *J. Am. Soc. Nephrol* 13:293-301.
Bernhardt et al. (1996) "Changes in IP$_3$ and cytosolica CA$^{2+}$ in response to sugards and non-sugar sweeteners in transduction of sweet tast in the rat" *J. Physiol* 490:325-336.
Bowie et al. (1990) "Deciphering the Message in Protein Sequences: Tolerance to Amino Acid Substitutions" *Science* 247:1306-1310.
Doolin et al. (1996) "Distribution and Characterization of Functional Amiloride-sensitive Sodium Channels in Rat Tongue" *J. Gen. Physiol.* 107: 545-554.

Gilbertson et al., "The molecular physiology of taste transduction" *Curr. Opin. Neurobiol.* 10; 519-527, 2000.
Hoon et al. (1999) "Putative mammalian taste receptors: a class of taste-specific GPCRs with distinct topographic selectivity" *Cell* 96:541-51.
Kinnamon et al., (1992) "Chemosensory transduction mechanisms in taste" *Annu. Rev. Physiol.* 54:715-731.
Lin and Corey (2005) "TRP channels in mechanosensation" *Curr Opin Neurobiol.* 15(3):350-7.
Lindemann (1996) "Taste reception" *Physiol. Rev.* 76:718-766.
Liu et al. (2003) "Intracellular Ca$^{2+}$ and the phospholipids PIP$_2$ regulate the taster transduction ion channel TRPM5" *Proc. Natl. Acad. Sci.* USA 100(25): 15160-15165.
Madden et al. (1997) "Taste Perception in Cirrhosis: Its Relationship to Circulating Micronutrients and Food Preferences" *Hepatology* 26(1): 40-48.
Margolskee (1993) "The molecular biology of taste transduction" *R. Bioessays* 15, 645-650.
Mueller et al. (2005) "The receptors and coding logic for bitter taste" *Nature* 434 (7030): 225-9.
Nauli and Zhou 2004 "Polycystins and Mechanosensation in renal and nodal cilia" *Bioessays* 26.8 844-856.
Nelson et al. (2001) "Mammalian sweet taste receptors" *Cell* 106(3): 381-90.
Nelson et al. (2002) "An amino-acid taste receptor" *Nature* 416(6877): 199-202.
Nomura, et al. (1998) "Identification of PKDL, a novel polycystic kidney disease 2-like gene whose murine homologue is deleted in mice with kidney and retinal defects" *J. Biol. Chem.* 273:25967-25973.
Ogura et al. (1997) "Bitter Taste Transduction of Denatonium in the Mudpuppy Necturus Maculosus," *J. of Neuroscience*, 17(10): 3580-3587.
Roper et al. (1989) "Distribution of Ion Channels on Taste Cells and Its Relations to Chemosensory Transduction," *J. Membrane Biology* 109(1):29-39.
Roper (1989) "The cell biology of vertebrate taste receptors" *Ann. Rev. Neurosci.* 12:329-353.
Wu et al. (1998) "Identification of PKD2L, a Human PKD2-Related Gene: Tissue-specific Expression and Mapping to Chromosome 10q25" *Genomics* 54(3) 564-568.
Zhang et al. (2003) "Coding of sweet, bitter, and umami tastes: different receptor cells sharing similar signaling pathways" *Cell* 112(3):293-301.
Zhao et al. (2003) "The receptors for mammalian sweet and umami taste" *Cell* 115(3):255-66.

* cited by examiner

*Primary Examiner*—Lorraine Spector
*Assistant Examiner*—Elly-Gerald Stoica
(74) *Attorney, Agent, or Firm*—Quine Intellectual Property Law Group, P.C.; Jonathan Alan Quine

(57) ABSTRACT

Taste receptor polycystin-2L1 is provided. Methods and systems for screening for tastants and receptor modulators are provided. Knock out and transgenic animals, methods of detecting polymorphisms, and methods of correcting taste defects are also provided.

29 Claims, 2 Drawing Sheets

Figure 2

METHOD OF IDENTIFYING ACTIVITY MODULATORS OF A POLYCYSTIN-2L1 TASTE RECEPTOR POLYPEPTIDE

FIELD OF THE INVENTION

The invention includes the discovery that polycystin-2L1 is a taste receptor protein. Polycystin-2L1 is a transmembrane ion channel protein encoded by the gene PKD2L1.

BACKGROUND OF THE INVENTION

Taste transduction is one of the most sophisticated forms of chemotransduction in animals (Avenet and Lindemann, 1989; Margolskee, 1993; Lindemann, *Physiol. Rev.* 76:718-766, 1996; Kinnamon et al., *Annu. Rev. Physiol.* 54:715-731, 1992; and Gilbertson et al., *Curr. Opin. Neurobiol.* 10: 519-527, 2000). Gustatory signaling is found throughout the animal kingdom, from simple metazoans to the most complex of vertebrates; its main purpose is to provide a reliable signaling response to non-volatile ligands.

Mammals are believed to have five basic types of taste modalities: salty, sour, sweet, umami (the taste of MSG), and bitter. Each of these is thought to be mediated by distinct signaling pathways leading to receptor cell depolarization, generation of a receptor or action potential and release of neurotransmitter and synaptic activity (Roper, ARN, 1989).

In general, the identification of new taste receptors is highly desirable. The identification of a taste receptor provides methods and systems for screening for new tastants, such as the identification of new artificial tastants (sweeteners, sour flavors, salt substitutes, etc.) and for the identification of activity modulators that produce a greater receptor response to specified amounts of a tastant. For example, the ability to modulate activity of the (previously unknown) salt receptor would be highly desirable, e.g., to provide a perception of salt flavor with minimal amounts of salt. This would have clear benefits for patients that suffer from hypertension, obesity, or other diseases that utilize reduced sodium intake as part of patient treatment. The use of sour or other flavor enhancers may also be useful in reducing the amount of sour or other flavoring needed to provoke a sour receptor taste cell response, which may thus be useful as a flavor enhancer.

Relatively recently, the receptors for bitter, sweet and umami were cloned and shown to be encoded by two families of G-protein coupled receptors (Nelson et al., 2000; Nelson et al., 2001; Zhang et al., 2003; Zhao et al., 2003; Mueller et al., 2005). In contrast, most of the molecular components of the sour and salty pathways remain unknown. Electrophysiological studies suggest that sour and salty tastants modulate taste cell function by direct entry of $H^+$ and $Na^+$ ions through specialized membrane channels on the apical surface of the cell. Thus, ion channels selectively expressed in taste receptor cells are likely candidates for mediators of salt and sour tastes. Alternatively, ion channels can function as a final critical signaling component in the activation of taste cells (akin to the role of TRPM5 in sweet, umami and bitter cells; Zhang et al., 2003).

Many other families of cell receptors are also known to function in a variety of signal transduction events associated with cell sensation. For example, the polycystins (e.g., PC1 and PC2, encoded by PKD1 and PKD2, respectively) are integral membrane proteins with large extracellular N termini that are thought to comprise a number of functions, including mechanosensation in renal and nodal cilia (reviewed in Nauli and Zhou 2004 "Polycystins and Mechanosensation in renal and nodal cilia" *Bioessays* 26.8 844-856 *Wiley Periodicals).*

The polycystins fall into two basic classes of proteins, the *PC*-1-like proteins, which are receptor-like molecules and the PC-2-like proteins, which are ion channels. Several studies have found overlapping and interdependent roles for these proteins in various systems, particularly in kidney cells.

SUMMARY OF THE INVENTION

The invention includes the surprising discovery that the PC-2-like protein polycystin-2L1, encoded by PKD2L1, is a taste receptor protein. Previously, this protein was though to be primarily involved in kidney function. This surprising discovery provides a receptor target for tastant and activity modulator identification and for studies on any taste-related behavioral effects mediated by polycystin-2L1. These assays can be cell based, e.g., screening of transgenic cells expressing PKD2L1 for receptor activity in response to test compounds, or can be behaviorally based on whole animal studies. For animals studies, transgenic non-human animals (e.g., mice) can be produced, including PKD2L1 knock-outs and transgenic animals comprising heterologous PKD2L1 genes, e.g., to facilitate behavioral and tastant studies for a PKD2L1 gene of interest. For example, a PKD2L1 knock-out mouse can be made transgenic with the PKD2L1 gene from a human, and the resulting transgenic mouse used to study responses to putative human polycystin-2L1 tastants and activity modulators. In addition, the invention provides for the identification of taste-receptor defects at the molecular level (e.g., thorough detection of PKD2L1 polymorphisms) and for the correction of these defects by gene therapy. Corresponding systems and kits are also included. Further details regarding these and other features of the invention are found below.

In one aspect, methods of screening a test compound, such as a putative tastant or modulator of activity of polycystin-2L1, are provided. In the methods, a compound that binds to or modulates an activity of a polycystin-2L1 taste receptor polypeptide is provided. A biological or biochemical sample comprising the polycystin-2L1 taste receptor polypeptide is contacted with a test compound and binding of the test compound to the polycystin-2L1 taste receptor polypeptide, or modulation of the activity of the polypeptide by the test compound is detected. This identifies whether the compound binds to or modulates the activity of the polycystin-2L1 taste receptor polypeptide.

Typically, the methods can be used in a high throughput fashion to screen one or more biological sample comprising one or more polycystin-2L1 taste receptor polypeptide with a plurality of test compounds. Binding of the test compounds to the polycystin-2L1 taste receptor polypeptide, or modulation of the activity of the polypeptide by the test compounds is detected, e.g., in a high throughput screen, thereby identifying compounds that bind to or modulate the activity of the polycystin-2L1 taste receptor polypeptide.

The test compounds can be from a pre-screened library, e.g., of compounds prescreened for any property of interest (toxicity, ingestibility, three dimensional chemical structure, type of molecule (ion, natural product, etc.)). For example, the test compounds can be, e.g., selected from libraries of naturally occurring compounds, ions, known salt or sour flavoring substitutes and analogues thereof, small organic molecules, peptides, peptide mimetics, weak acids, $CO_2$, acetic acid, specific blockers of carbonic anhydrases such as MK-417, and/or the like. Whether identified from a pre-screened or random collection of compounds, any compound that is identified as having a desired activity in any screen herein can be further modified to reduce toxicity, enhance activity, or the like.

The precise activity of the test compound on polycystin-2L1 can vary. In one embodiment, the test compound enhances an activity of the polycystin-2L1 taste receptor polypeptide. Alternately, the test compound can potentiate an activity of the polycystin-2L1 taste receptor polypeptide. The test compound can inhibit or block an activity of the polycystin-2L1 taste receptor polypeptide.

For any assay herein, suitable sources of polycystin-2L1 are available, e.g., human, rat, dog or murine polycystin-2L1 taste receptor polypeptides (or PKD2L1 genes that encode such polypeptides).

In addition, transgenic livestock or domesticated animals can be made recombinant for a given polycystins-2L1 polypeptide, or a modified form thereof, thereby changing the feeding behavior of the transgenic animal, e.g., to enhance yield of a domesticated or livestock animal.

In a preferred embodiment, the assay methods of the invention are cell-based, or use preparations of cellular materials. In these embodiments, the biological sample comprises or is derived from a cell that expresses the polycystin-2L1 taste receptor polypeptide. Most typically, such cells are provided by expressing a PKD2L1 gene in a recombinant cell. The PKD2L1 gene is typically, though not necessarily, heterologous to the recombinant cell.

The cell is typically selected for ease of manipulation and convenience of the practitioner and can be, e.g., a human, rodent, *Xenopus* or insect cell, and can be a cell in culture or a primary cell. The cell can also be, e.g., a taste bud or kidney cell, or can be derived from a taste bud or kidney cell, e.g., where receptor activity is to be studied in a cellular context similar to one in which the receptor is expressed in vivo. Typically, however, the cell can be any cell typically used in culture, e.g., a mammalian cell (e.g., CHO), an insect cell (e.g., Snyder or KT), a *Xenopus* oocyte, or the like.

In the methods, whether a cell based or cell free format is used, binding can be detected between the polycystin-2L1 taste receptor polypeptide and a test compound moiety such as a potentiator of the polycystin-2L1 taste receptor polypeptide, an antagonist of the polycystin-2L1 taste receptor polypeptide, an agonist of the polycystin-2L1 taste receptor polypeptide, an inverse agonist of the polycystin-2L1 taste receptor polypeptide, a ligand that specifically binds to the polycystin-2L1 taste receptor polypeptide, and/or an antibody that specifically binds to the polycystin-2L1 taste receptor polypeptide.

In general, detection of polycystin-2L1 binding or activity can be performed in vitro, in situ or in vivo. Typically, a signal resulting from the binding or activity of the polycystin-2L1 taste receptor polypeptide is detected. Such signals that can be detected include polycystin-2L1 conformation-dependent signals, e.g., where a conformation of the polycystin-2L1 taste receptor polypeptide is modified by binding of the test compound to the polycystin-2L1 taste receptor polypeptide. Other detection modalities that can be used include detecting one or more of: $H^+$ flux, $Na^+$ flux, $Ca^{2+}$ flux, ion flux, depolarization of a cell, cell membrane voltage changes, cell membrane conductivity changes, a kinase activity triggered upon binding of a compound to the polycystin-2L1 taste receptor polypeptide, generation, breakdown or binding of a phorbol ester by the polycystin-2L1 taste receptor polypeptide, binding of diacylglycerol or other lipids by the polycystin-2L1 taste receptor polypeptide, cAMP activity, cGMP activity, GTPgammaS binding, phospholipase C activity, activity of an enzyme involved in cellular ionic balance, binding of polycystin-2L1 to a PC-1 like or PC-2 like protein (including PC-1 or PC-2), formation of homo or heterodimers, e.g., with other polycystin proteins, or a transcriptional reporter activity.

In one optional aspect, the polycystin-2L1 taste receptor polypeptide can be incorporated into a biosensor, e.g., for detection of compounds that activate or bind to the polycystin-2L1 taste receptor polypeptide. This can be used as a component of an artificial device, e.g., for chemodetection. For example, in one implementation, the biosensor comprises a Chem-FET operably coupled to the polycystin-2L1 taste receptor polypeptide.

Systems for practicing the methods herein are also a feature of the invention. For example, systems for detecting compounds that bind to or modulate an activity of a polycystin-2L1 taste receptor polypeptide are provided. In one implementation, the system includes a biological sample comprising the polycystin-2L1 taste receptor polypeptide and a source of a plurality of test compounds. Typically, the system further includes a detector that detects binding of one or more of the test compounds to the polycystin-2L1 taste receptor polypeptide, or modulation of the activity of the polypeptide by one or more of the test compounds, thereby identifying a putative tastant compound that binds to or modulates the activity of the polycystin-2L1 taste receptor polypeptide.

Features noted above for the method claims are applicable here as well, e.g., use of various cells or cell components to provide or constitute the biological sample, e.g., a cell comprising a heterologous gene encoding the polycystin-2L1 taste receptor polypeptide. Example cells include mammalian cells, insect cells, *Xenopus* cells, taste receptor cells, kidney cells, and the like. Similarly as above, the taste receptor or modulator can include any activity modulating compound, e.g., an agonist, enhancer, antagonist, or inverse agonist.

The source of test compounds optionally comprises a library of tastant compounds, e.g., any of those already noted, e.g., of small molecules that cover a large amount of chemical diversity, a library natural compounds, a library of peptides or peptidomimetics, a library pre-screened for compounds of a given activity or structure, etc. The format of the source can be, e.g., a multi-well plate, a microfluidic device, a solid phase array, or the like.

The detector optionally includes a voltage or patch clamp device or an optical detection device. In one implementation, the detector includes a flourescence detector that detects FRET, changes in membrane potential or flow of a dye into or out of the cell. Patch clamping, FRET based sensors, transmembrane flow of ion sensitive dyes, expression in oocytes and voltage clamping are all useful embodiments.

In another aspect, methods of detecting a taste-induced behavior modulated by a polycystin-2L1 taste receptor polypeptide are provided. The methods include introducing a heterologous PKD2L1 taste receptor gene into an animal and expressing an encoded heterologous polycystin-2L1 taste receptor polypeptide in a taste bud of the animal. A putative polycystin-2L1 taste receptor tastant or modulator is provided to the animal, and a feeding behavior of the animal is monitored in response to the presence of the putative polycystin-2L1 taste receptor tastant.

Optionally, the gene includes a heterologous promoter that is active in the taste bud of the animal. Examples of heterologous promoters includes a polycystin-2L1 taste receptor gene promoter, a T1R-gene promoter, T2R-gene promoter, TRPM5-gene promoter, a PLCB2 gene promoter, a repeater gene promoter, a gustducin gene promoter, a Gi2 gene promoter, a cytokeratin-19 gene promoter, and/or a promoters for a gene that is naturally selectively expressed in a taste receptor cell of the tongue or palate epithelium.

Optionally, the animal is a mouse or other commonly used laboratory animal (rat, rabbit, etc.) and the heterologous PKD2L1 taste receptor gene is a human PKD2L1 taste receptor gene. The animal optionally is a knock out animal for an endogenous PKD2L1 taste receptor gene. The recombinant (e.g., transgenic) animal thus optionally provides the human PKD2L1 taste receptor gene in an animal model, providing one of skill with a model system for detecting the behavioral influence of test compounds on the human receptor in an established animal model.

Many formats for detecting taste-induced behavior modulated by the polycystin-2L1 taste receptor polypeptide are provided. In one example format, a putative polycystin-2L1 taste receptor tastant or modulator is provided on a licking or feeding device (licking stick, solution with the tastant or modulator, food with the tastant of modulator, etc.) to the animal and licking or feeding behavior of the animal on the device is monitored. Typically, in this or other formats, the putative polycystin-2L1 taste receptor tastant or modulator is provided to the animal in conjunction with a control compound and the relative frequency of feeding behavior between the putative polycystin-2L1 taste receptor tastant and the control compound is determined.

Systems for practicing the methods are also a feature of the invention. For example, the system can include a non-human animal comprising a heterologous PKD2L1 taste receptor gene that is expressed in a taste bud of the animal. The system can further include a source of a putative polycystin-2L1 taste receptor tastant that is accessible to the animal and a detector that detects a feeding behavior of the animal in response to the presence of the putative polycystin-2L1 taste receptor tastant.

The detector optionally comprises a camera that detects movement by the animal. An analysis module operably linked to the detector analyzes information received from the detector.

In yet another aspect, the invention includes a recombinant taste bud cell comprising a heterologous PKD2L1 taste receptor gene, or a heterologous polycystin-2L1 taste receptor polypeptide. Typically, the taste bud cell is in culture, or is present in a recombinant non-human animal.

Similarly, a knock out non-human animal (e.g., a mouse) comprising a defect in a native PKD2L1 taste receptor gene or a defect in native PKD2L1 gene expression is a feature of the invention. Optionally, the animal comprises a heterologous PKD2L1 taste receptor gene (e.g., a human PKD2L1 taste receptor gene) that is expressed in the taste-bud of the animal.

Methods of detecting a molecular basis for a taste receptor function abnormality are also provided. The methods include determining whether a biological sample from a patient comprises a polymorphism in a gene encoding polycystin-2L1 or an abnormality in expression of polycystin-2L1. The polymorphism (e.g., a SNP) is then correlated with an abnormality in taste receptor function, thereby determining whether the patient has a genetic basis for a taste receptor function abnormality. The abnormality in expression of polycystin-2L1 can include, e.g., an abnormal tissue distribution of polycystin-2L1 mRNA or protein.

In another aspect, a method of rescuing a taste bud cell that has altered or missing polycystin-2L1 taste receptor function is provided. The method includes introducing a nucleic acid encoding the recombinant polypeptide homologous to polycystin-2L1 into the cell, and expressing the recombinant polypeptide, thereby providing polycystin-2L1 function to the cell. The cell can be in cell culture, in a tissue, in a taste bud, in a mammal, etc.

Kits for practicing the above methods are also a feature of the invention. The kits can include, e.g., a PKD2L1 nucleic acid, e.g., a vector comprising a PKD2L1 gene, a polycystin-2L1 polypeptide, recombinant cells expressing the gene or polypeptide, transgenic animals, etc., as noted above. The kits can further include instructions for using the other kit components to practice the methods herein, system components, packaging materials for packaging the components noted above, etc.

BRIEF DESCRIPTION OF THE FIGURES

FIG. 2 provides an alignment of sequences for human (SEQ ID NO:8), rat (SEQ ID NO:6), and mouse (SEQ ID NO:7) PKD2L1. The predicted amino acid sequence corresponding to the fragment isolated from mouse taste tissue is also included in the alignment (SEQ ID NO:2).

DEFINITIONS

Figure 1:
FIG. 1 shows results from the RNA in situ hybridization in circumvallate taste papillae.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

A "polycystin-2L1 taste receptor polypeptide" is a polypeptide that is the same as, a splice-variant of, or homologous to a human polycystin-2L1 or murine polycystin-2L1 and that is expressed in taste receptor cells, or that is derived from such a polypeptide that is expressed in such taste receptor cells (e.g., through cloning, recombination, mutation, or the like). The polypeptide can be full length or can be a fragment of a full length protein. A polycystin-2L1 fragment typically includes at least 10 contiguous amino acids corresponding to a native polycystin-2L1 protein, such as a human murine, dog or rat polycystin-2L1. The polycystin-2L1 taste receptor polypeptide can be naturally occurring or recombinant, and can be unpurified, purified, or isolated, and can exist, e.g., in vitro, in vivo, or in situ. In one typical useful embodiment, the polycystin-2L1 taste receptor polypeptide is a transmembrane protein.

A "PKD2L1 gene" is a nucleic acid that encodes a polycystin-2L1 polypeptide. Typically, the gene includes regulatory sequences that direct expression of the gene in one or more cells of interest. Optionally, the PKD2L1 gene is a native gene that includes regulatory and coding sequences that naturally direct expression of a polycystin-2L1 polypeptide.

A biological sample comprising the polycystin-2L1 taste receptor polypeptide includes any sample comprising the polycystin-2L1 taste receptor polypeptide that is derived from a biological source, e.g., cells, tissues, organisms, cells, secretions, etc. These samples can include, e.g., cells expressing the receptor, membranes containing the receptor, receptor bound to a chemical matrix, receptor bound to solid surface (e.g., for plasmon resonance), etc. A biochemical source can include biological sources and/or non-biological sources, such as purely synthetic preparations of materials.

A "tastant" is a compound that can be tasted by the relevant organism. These typically include compounds that can stimulate or inhibit one or more activity of one or more taste receptor, taste cells or other sensory cells and/or nerves in the oral cavity. A tastant can be any molecule, including ions, peptides, nucleotides, natural compounds, small organic molecules, etc. that leads to modulation of taste receptor or taste cell activity or a change taste cell function either on its own or in the presence of other compounds.

A taste receptor "modulator" is a compound that modulates an activity of a taste receptor, e.g., in response to a tastant. The term "modulate" with respect to a polycystin-2L1 polypeptide refers to a change in an activity or property of the polypeptide. For example, modulation can cause an increase or a decrease in a protein activity, a binding characteristic, membrane permeability or any other biological, functional, or immunological properties of such proteins. The change in activity can arise from, for example, an increase or decrease in expression of one or more genes that encode these proteins, the stability of an mRNA that encodes the protein, translation efficiency, or from a change in activity of the protein itself. For example, a molecule that binds to polycystin-2L1 can cause an increase or decrease in a biological activity of the polypeptide. Example modulators include polycystin-2L1 allosteric enhancers, agonists, antagonists, inverse agonists, or partial agonists, polycystin-2L1 ligands, antibodies to polycystin-2L1, etc.

A "prescreened" compound is a compound that is preselected for a property of interest, such as toxicity, lack of toxicity, bioavaliability, chemical structure, type of molecule (natural product, ion, ion channel agonist/antagonist/inverse agonist, etc.), or the like. For example, an "ingestible compound" is a compound that can be safely ingested in an amount that triggers a taste receptor or taste cell response by the compound. Certain compounds such as agonists or enhancers can have such a desired response when present at very low doses, while others are present in higher amounts. In addition, certain ingestible compounds such as enhancers optionally have no taste of their own, but enhance the action of natural or chemically synthesized tastants on a taste receptor or taste cell.

A "transmembrane potential" is the work needed to move a unit of charge across a membrane such as a cell membrane.

A "cationic membrane permeable dye" is a dye which has a positive charge under specified pH (e.g., physiological pH) where the dye can cross a selected membrane such as the membrane of an intact cell.

An "anionic membrane permeable dye" is a dye which has a negative charge at a specified pH (e.g., physiological pH) and which is membrane permeable and whose distribution between the inside and outside of the space bounded by the membrane or between the inside and outside of the membrane, depends on the transmembrane potential across the membrane.

A "neutral dye" has an overall neutral charge under the relevant conditions at issue, e.g., a specified pH (e.g., physiological pH).

A "voltage sensing composition" is a transmembrane potential indicator, e.g., comprising a fluorescent dye. Common voltage sensing compositions of the invention include one or more cationic or anionic membrane permeable dye(s).

A membrane is "depolarized" when the transmembrane potential across the membrane becomes more positive inside. A membrane is "hyperpolarized" when the transmembrane potential becomes more negative inside.

A membrane is "permeable" to a given component (dye, ion, etc.) when that component can cross the membrane. Permeability can be dependent upon the relevant conditions, e.g., temperature, ionic conditions, voltage potentials, or the like.

DETAILED DESCRIPTION

The ability to screen taste receptors for response to tastant stimuli is of considerable commercial utility. Libraries of putative tastant compounds can be screened for activity against a given receptor to identify taste enhancers, sour tastants, salt substitutes, and the like. The identification of new salt, sour or other tastants is of value, e.g., to provide new flavors that can be added to foods and drinks. Similarly, compounds that modulate activity of a receptor can be used to make the receptor more (or less) sensitive to a tastant, which is particularly valuable when considering responsiveness to salt or other tastants that have associated health consequences upon consumption. For example, by reducing the amount of salt that is needed to trigger a response for a salt receptor by applying an appropriate receptor modulator to the receptor, a patient on a low sodium diet can experience the desirable mouth feel and flavor sensation of a higher salt diet, without actually consuming high levels of salt. In one aspect of the invention, polycystin-2L1 is tested for responsiveness to salt, or to other tastants such as sour compounds, and tastants or modulators of the receptor are identified.

Given the identification of polycystin-2L1 as a taste receptor protein herein, there are several ways in which this protein can now be screened for responsiveness to test compounds (tastants, activity modulators, etc.), including in high-throughput cell-based assays, in animal behavioral models (e.g., using transgenic animals that express a human or other desirable heterologous polycystin-2L1 polypeptide), or the like. Polymorphisms in the gene for polycystin-2L1 (PKD2L1) can also be detected to provide a molecular test for tasting disorders and defects in PKD2L1 can be rescued by gene therapy. In this regard, administration of a gene therapy vector to the tastebud is relatively simple, due to ready access to this tissue, and can be targeted to a considerable degree simply by controlling the site of vector administration. Systems and kits for practicing the methods, transgenic animals (PKD2L1 knock-outs and/or transgenics), and related features are also included within the scope of the invention. Further details regarding these various features of the invention are found herein, e.g., below.

Screening Test Compounds for Activity Against Polycystin-2L1

In one aspect, methods of identifying a compound that binds to or modulates an activity of a polycystin-2L1 taste receptor polypeptide are provided. In these methods, a biological or biochemical sample comprising the polycystin-2L1 taste receptor polypeptide is contacted with a test compound and binding of the test compound to the polycystin-2L1 taste receptor polypeptide, or modulation of the activity of the polypeptide by the test compound is detected, thereby identifying the compound which binds to or modulates the activity of the polycystin-2L1 taste receptor polypeptide.

Desirably, a test compound can be, e.g., a potentiator or enhancer of the polycystin-2L1 taste receptor polypeptide, an antagonist of the polycystin-2L1 taste receptor polypeptide, an agonist of the polycystin-2L1 taste receptor polypeptide, an inverse agonist of the polycystin-2L1 taste receptor polypeptide, a ligand that specifically binds to the polycystin-2L1 taste receptor polypeptide, an antibody that specifically binds to the polycystin-2L1 taste receptor polypeptide, or the like.

Additional Details Regarding Screening Methods

High throughput methods of screening are particularly useful in identifying tastants or modulators of polycystin-2L1 taste receptor polypeptide activity, and/or of PKD2L1 gene expression. Generally in these methods, one or more biological sample that includes one or more polycystin-2L1 taste receptor polypeptide is contacted with a plurality of test compounds. Binding to polycystin-2L1 or modulation of the polycystin-2L1 taste receptor polypeptide by the test compounds is detected, thereby identifying one or more compound that binds to or modulates the activity of the polycystin-2L1 taste receptor polypeptide.

Essentially any available compound library can be screened in such a high-throughput format against a biological or biochemical sample, such as a cell expressing a polycystin-2L1 taste receptor polypeptide, and activity of the library members against the polycystin-2L1 taste receptor polypeptide or expression thereof can be assessed in a high-throughput fashion.

Many libraries of compounds are commercially available, e.g., from the Sigma Chemical Company (Saint Louis, Mo.), Aldrich chemical company (St. Louis Mo.), and many can be custom synthesized by a wide range of biotech and chemical companies. A variety of proprietary libraries also exist, including those specifically designed for screening of taste receptors, e.g., from Senomyx, Inc. (La Jolla Calif.).

In one desirable aspect, the plurality of test compounds comprise a plurality of compounds. Thus, the library to be screened can include a previously unscreened library of compounds, or can include a pre-screened library of compounds that are pre-screened for any property that is desired, e.g., toxicity, bioavialability, chemical structure, known activity (e.g., ion channel binding or modulating activity) ingestibility, or the like. Further details on available libraries are found below.

In general, test compounds that enhance or potentiate an activity of the polycystin-2L1 taste receptor polypeptide are particularly desirable and can be screened for using the methods of the invention. However, test compounds that inhibits or block an activity of the polycystin-2L1 taste receptor polypeptide are also desirable, e.g., where the taste sensation associated with a flavor would benefit from reduced responsiveness (e.g., in those cases where more than usual of the tastant is desirably consumed).

Additional Details Regarding Assay Formats

In another aspect, the present invention relates to the use of the polycystin-2L1 polypeptides and/or coding nucleic acids in methods for identifying a compound, e.g., a tastant, that interacts/binds to the polypeptide. The test compound can be natural or synthetic molecules such as ions, proteins or fragments thereof, carbohydrates, organic or inorganic compounds and/or the like. For example, the test compounds can be naturally occurring compounds, ions, salt or sour substitutes, small organic molecules, peptides, peptide mimetics, a weak acid, $CO_2$, acetic acid, a specific blocker of carbonic anhydrase, MK-417, etc. This can be achieved, e.g., by utilizing the polypeptides of the invention, including active fragments thereof, in cell-free or cell-based assays. A variety of formats are applicable, including measurement of second messenger effects (e.g., $H^+$ flux, $Na^+$ flux, $Ca^{2+}$ flux, ion flux, depolarization of the cell, cell membrane voltage changes, cell membrane conductivity changes, a kinase activity triggered upon binding of a compound to the polycystin-2L1 taste receptor polypeptide, generation, breakdown or binding of a phorbol ester by the polycystin-2L1 taste receptor polypeptide, binding of diacylglycerol or other lipids by the polycystin-2L1 taste receptor polypeptide, cAMP activity, cGMP activity, GTPgammaS binding, phospholipase C activity, activity of an enzyme involved in cellular ionic balance, binding of polycystin-2L1 to another PKD protein, or a transcriptional reporter activity assay, e.g., using CRE, SRE, MRE, TRE, NFAT, and/or NFkB-response elements coupled to appropriate reporters.

In one embodiment, cell-free assays for identifying such compounds comprise a reaction mixture containing a polycystin polypeptide encoded by one of the disclosed genes and a test compound or a library of test compounds. Accordingly, one example of a cell-free method for identifying test compounds that specifically bind to polycystin 2-L1 comprises contacting a protein or functional fragment thereof with a test compound or library of test compounds and detecting the formation of complexes by conventional methods. In one class of useful embodiments, a library of the test compounds can be synthesized on a solid substrate, e.g., a solid surface, plastic pins or some other surface. The test compounds are reacted with the polypeptide and washed to elute unbound polypeptide. Bound polypeptide is then detected by methods well known in the art. A reciprocal assay can also be used, e.g., in which polypeptide is applied directly onto plates and binding of the test compound to the polypeptide is detected. Antibody or ligand binding to the polypeptide can also be detected in either format.

Interaction between molecules can also be assessed using real-time BIA (Biomolecular Interaction Analysis, e.g., using devices from Pharmacia Biosensor AB), which detect surface plasmon resonance (an optical phenomenon). Detection depends on changes in the mass concentration of macromolecules at the biospecific interface and does not require specific labeling of the molecules. In one useful embodiment, a library of test compounds can be immobilized on a sensor surface, e.g., a wall of a micro-flow cell. A solution containing the polycystin-2L1 polypeptide is then continuously circulated over the sensor surface. An alteration in the resonance angle, as indicated on a signal recording, indicates the occurrence of an interaction. This general technique is described in more detail in the *BIAtechnology Handbook* by Pharmacia.

Optionally, the polycystin-2L1 polypeptide is immobilized to facilitate separation of complexes between the polycystin-2L1 polypeptide and a test compound from uncomplexed forms of the polycystin-2L1 polypeptide. This also facilitates automation of the assay. Complexation of polycystin-2L1 polypeptide can be achieved in any type of vessel, e.g., microtitre plates, microfluidic chambers or channels, microcentrifuge tubes and test tubes. In one embodiment, the polycystin-2L1 polypeptide is fused to another protein, e.g., glutathione-S-transferase to form a fusion protein which can be adsorbed onto a matrix, e.g., glutathione Sepharose™ beads (Sigma Chemical. St. Louis, Mo.), which are then combined with the test compound and incubated under conditions sufficient to form complexes. Subsequently, the beads are washed to remove unbound label, and the matrix is immobilized and the radiolabel is determined.

Similar methods for immobilizing proteins on matrices use biotin and streptavidin. For example, the protein can be biotinylated using biotin NHS (N-hydroxy-succinimide), using well known techniques and immobilized in the well of streptavidin-coated plates.

Cell-free assays can also be used to identify tastants or other compounds that bind and/or modulate the activity of a polycystin-2L1 polypeptide. In one embodiment, the polycystin-2L1 polypeptide is incubated with a test compound and the transmembrane ion channel activity of the protein is determined. In another embodiment, the binding affinity of the protein to a target molecule is determined by standard methods.

Further Details Regarding Cell Based Assays

In addition to cell-free assays such as those described above, the polycystin-2L1 polypeptide can be used in cell-based assay for identifying compounds that bind to, activate and/or modulate polycystin-2L1 polypeptide activity.

For example, one method for identifying compounds which bind to polycystin-2L1 polypeptides comprise providing a cell that expresses one of these proteins, e.g., a human polycystin-2L1 polypeptide, combining a test compound with the cell and measuring the formation of a complex between the test compound and the human polycystin-2L1 polypeptide. The cell can be a mammalian cell (e.g., a CHO cell), a yeast cell, a bacterial cell, an insect cell, a Xenopus oocyte, a human or other mammalian taste cell, a kidney cell or any other cell expressing the polycystin-2L1 polypeptide, whether that expression is natural to the cell or the result of recombinant introduction of a PKD2L1 gene of interest. Further details regarding appropriate cells is found below.

In another embodiment, taste cells or cells expressing heterologous polycystin-2L1 polypeptides, or membrane preparations of such cells, can be utilized to screen for bioactivity of test compounds. The polycystin-2L1 polypeptides described herein are $Ca^{2+}$ permeable cation selective channels (pore forming channels). In addition, G-proteins such as PC-1 and PC1-like proteins also interact with polycystin-2 proteins and may interact with polycystin-2L1 polypeptides. A variety of intracellular effectors have been identified as being $Ca^{2+}$/G-protein regulated including, but not limited to, $Ca^{2+}$-induced intraorganellar $Ca^{2+}$ release by ryanodine and/or IP3 receptors, adenyl cyclase, cyclic GMP, phospholipase C, phospholipase A2 and phosphodiesterases, etc. Accordingly, the level of such second messengers produced by the aforementioned intracellular effectors, and thus activity of polycystin-2L1 polypeptides, can be measured by techniques that are well known. For example, the level of cAMP produced by activation of adenyl cyclase can be measured by assays which monitor cAMP, either in vivo by using FRET or transcriptional reporters sensitive to cAMP, or in vitro by directly measuring cAMP production. The GTPase activity by G proteins can be measured, e.g., in plasma membrane preparations by measuring the hydrolysis of gamma $^{32}P$ GTP, or in vivo by FRET or by monitoring activity of downstream effectors such as PLC, adenylate cyclase, etc. Breakdown of phosphatidylinositol-4,5-bisphosphate to 1,4,5-IP3 and diacylglycerol can be monitored by measuring the amount of diacylglycerol using thin-layer chromatography, or measuring the amount of IP3 using radiolabeling techniques or HPLC, or in vivo by activation of the IP3 receptor and release of calcium from internal stores. The generation of arachidonic acid by the activation of phospholipase A2 can be readily quantitated by well-known techniques.

Efflux of intracellular calcium or influx of calcium from outside the cell can be measured using conventional techniques, e.g., loading cells with a $Ca^{++}$ sensitive fluorescent dye such as fura-2 or indol-1, and measuring any change in $Ca^{++}$ using a fluorometer, such as Fluoskan Ascent Fluorescent Plate Reader or Flurometric Imaging Plate Reader. The signal pathways initiated by polycystin-2L1 polypeptides in response to salt, sour or other compounds can also be monitored by reporter gene assays.

Assays that monitor changes in membrane potential by (1) voltage measurements in Xenopus oocytes injected with mRNA encoding PKD2L1, (2) patch clamping in tissue culture cells expressing the receptor, and (3) fluorometric assays using voltage-sensitive dyes or ionic fluxes are preferred assays for monitoring membrane potential in the context of the present invention.

In other aspects, interactions between polycystin 2L1 and related proteins are monitored to detect activity or binding properties of polycystin 2L1, or related complexes comprising polycystin 2L1. For example, PC2-like proteins (which are typically ion channels) often interact with PC-1 like proteins (which are typically G-proteins) to provide functional receptor complexes. In addition, homodimers and heterodimers between different PC-1 and PC-2 proteins can exist. Accordingly, binding between polycystin 2L1 and other polycystins can be monitored, e.g., by FRET or other protein-protein interaction technologies (cross-linking, etc.) to monitor homodimer and heterodimer formation, gating by PC-1 or PC-2 or related proteins, or the like.

As described, other assays such as melanophore assays, Phospholipase C assays, $Ca^{++}$mobilization assays, beta-arrestin FRET assays, and transcriptional reporter assays, e.g., using CRE, SRE, HE, TRE, NFAT, and/or NFkB-response elements coupled to appropriate reporters can be used. Detection using reporter genes coupled to appropriate response elements are particularly convenient. For example, the coding sequence to chloramphenicol acetyl transferase, beta galactosidase or other convenient markers are coupled to a response element that is activated by a second messenger that is activated by a protein of the invention, e.g., through $Ca^{++}$ release. Cells expressing the marker in response to application of an appropriate test compound are detected by cell survival, or by expression of a calorimetric marker, or the like, according to well established methods.

Any of a variety of potential modulators of polycystin-2L1 or PKD2L1 activity or expression can be screened for. For example, potential modulators (ions, salt or sour substitutes, small organic molecules, peptides, peptide mimetics, weak acids, $CO_2$, acetic acid, blockers of carbonic anhydrase, MK-417, small molecules, organic molecules, inorganic molecules, proteins, hormones, transcription factors, or the like) can be contacted to a cell and an effect on polycystin-2L1 polypeptide and/or PKD2L1 activity and/or expression monitored by any of the assays described herein or known in the art.

Furthermore, expression of PKD2L1 can be detected, e.g., via northern analysis or quantitative (e.g., real time) RT-PCR, before and after application of potential expression modulators. Similarly, promoter regions of and PKD2L1 gene of interest (e.g., generally sequences in the region of the start site of transcription, e.g., within 5 KB of the start site, e.g., 1 KB, or less e.g., within 500 BP or 250 BP or 100 BP of the start site) can be coupled to reporter constructs (CAT, beta-galactosidase, luciferase or any other available reporter) and can be similarly be tested for expression activity modulation by the potential modulator. In either case, the assays can be performed in a high-throughput fashion, e.g., using automated fluid handling and/or detection systems, in serial or parallel fashion. Similarly, activity modulators can be tested by contacting a potential modulator to an appropriate cell using any of the activity detection methods herein, regardless of whether the activity that is detected is the result of activity modulation, expression modulation or both.

In any of the assays herein, control compounds can be administered and the activity of the control compounds compared to those of the test compounds to verify that changes in activity resulting from application of the test compound are not artifacts. For example, control compounds can include the various dyes, buffers, adjuvants, carriers, or the like that the test compounds are typically administered with, but lacking a putative test compound.

Details Regarding Transmembrane Potential Measurements and Transmembrane Dyes

As noted above, the invention optionally includes monitoring transmembrane potential (TM potential) to track ion channel activity of polycystin 2L1. In general, the distribution of a permeable ion between the inside and outside of a cell or other membrane depends on the transmembrane potential of the cell membrane. In particular, for ions separated by a semi-permeable membrane, the electrochemical potential difference ($\Delta\mu_j$) which exists across the membrane, is given by $\Delta\mu_j$=2.3 RT log $[j_I]/[j_o]$+$zE_RF$, where R is the universal gas constant, T is an absolute temperature of the composition, F is Faraday's constant in coulombs, $[j_I]$ is the concentration of an ion (j) on an internal or intracellular side of the at least one membrane, $[j_o]$ is the concentration of j on an external or extracellular side of the at least one membrane, z is a valence of j and $E_R$ is a measured transmembrane potential. Thus, the calculated equilibrium potential difference ($E_j$) for ion j=−2.3 RT$(zF)^{-1}$ log $[j_I]/[j_o]$ (this is often referred to as the "Nernst equation"). See, Selkurt, ed. (1984) *Physiology 5$^{th}$ Edition*, Chapters 1 and 2, Little, Brown, Boston, Mass. (ISBN 0-316-78038-3); Stryer (1995) *Biochemistry 4$^{th}$ edition* Chapters 11 and 12, W. H. Freeman and Company, NY (ISBN 0-7167-2009-4); Haugland (1996) *Handbook of Fluorescent Probes and Research Chemicals Sixth Edition* by Molecular Probes, Inc. (Eugene Oreg.) Chapter 25 (Molecular Probes, 1996) and http://www.probes.com/handbook/sections/2300.html (Chapter 23 of the on-line 1999 version of the *Handbook of Fluorescent Probes and Research Chemicals Sixth Edition* by Molecular Probes, Inc.) (Molecular Probes, 1999) and Hille (1992) *Ionic Channels of Excitable Membranes*, second edition, Sinauer Associates Inc. Sunderland, Mass. (ISBN 0-87893-323-9) (Hille), for an introduction to transmembrane potential and the application of the Nernst equation to transmembrane potential. In addition to the Nernst equation, various calculations which factor in the membrane permeability of an ion, as well as Ohm's law, can be used to further refine the model of transmembrane potential difference, such as the "Goldman" or "constant field" equation and Gibbs-Donnan equilibrium. See Selkurt, ed. (1984) *Physiology 5$^{th}$ Edition*, Chapter 1, Little, Brown, Boston, Mass. (ISBN 0-316-78038-3) and Hille at e.g., chapters 10-13.

Increases and decreases in resting transmembrane potential—referred to as membrane depolarization and hyperpolarization, respectively—play a central role in many physiological processes, including ion-channel gating. Potentiometric optical probes (typically potentiometric dyes) provide a tool for measuring transmembrane potential and changes in transmembrane potential over time (e.g., transmembrane potential responses following the addition of a composition which affects transmembrane potential) in membrane containing structures such as organelles, cells and in vitro membrane preparations. In conjunction with probe imaging techniques (e.g., visualization of the relevant dyes), dye probes are used to map variations in transmembrane potential across cells membranes.

Potentiometric probes include cationic or zwitterionic styryl dyes, cationic rhodamines, anionic oxonols, hybrid oxonols and merocyanine 540. The class of dye determines factors such as accumulation in cells, response mechanism and cell toxicity. See, Molecular Probes 1999 and the reference cited therein; Plasek et al. (1996) "Indicators of Transmembrane potential: a Survey of Different Approaches to Probe Response Analysis." *J Photochem Photobiol*; Loew (1994) "Characterization of Potentiometric Membrane Dyes." *Adv Chem Ser* 235, 151 (1994); Wu and Cohen (1993) "Fast Multisite Optical Measurement of Transmembrane potential" *Fluorescent and Luminescent Probes for Biological Activity*, Mason, Ed., pp. 389-404; Loew (1993) "Potentiometric Membrane Dyes." *Fluorescent and Luminescent Probes for Biological Activity*, Mason, Ed., pp. 150-160; Smith (1990) "Potential-Sensitive Molecular Probes in Membranes of Bioenergetic Relevance." *Biochim Biophys Acta* 1016, 1; Gross and Loew (1989) "Fluorescent Indicators of Transmembrane potential: Microspectrofluorometry and Imaging." *Meth Cell Biol* 30, 193; Freedman and Novak (1989) "Optical Measurement of Transmembrane potential in Cells, Organelles, and Vesicles" *Meth Enzymol* 172, 102 (1989); Wilson and Chused (1985) "Lymphocyte Transmembrane potential and $Ca^{+2}$-Sensitive Potassium Channels Described by Oxonol Dye Fluorescence Measurements" *Journal of Cellular Physiology* 125:72-81; Epps et al. (1993) "Characterization of the Steady State and Dynamic Fluorescence Properties of the Potential Sensitive dye bis-(1.3-dibutylbarbituric acid)trimethine oxonol ($DiBAC_4(3)$) in model systems and cells" *Chemistry of Physics and Lipids* 69:137-150, and Tanner et al. (1993) "Flow Cytometric Analysis of Altered Mononuclear Cell Transmembrane potential Induced by Cyclosporin" *Cytometry* 14:59-69.

Potentiometric dyes are typically divided into at least two categories based on their response mechanism. The first class of dyes, referred to as fast-response dyes (e.g., styrylpyridinium dyes; see, e.g., Molecular Probes (1999) at Section 23.2), operate by a change in the electronic structure of the dye, and consequently the fluorescence properties of the dye, i.e., in response to a change in an electric field which surrounds the dye. Optical response of these dyes is sufficiently fast to detect transient (millisecond) potential changes in excitable cells, e.g., isolated neurons, cardiac cells, and even intact brains. The magnitude of the potential-dependent fluorescence change is often small; fast-response probes typically show a 2-10% fluorescence change per 100 mV.

The second class of dyes, referred to as slow-response (or "Nernstian") dyes (See, e.g., Molecular Probes, 1999 at Section 23.3), exhibit potential-dependent changes in membrane distribution that are accompanied by a fluorescence change. The magnitude of their optical responses is typically larger than that of fast-response probes. Slow-response probes, which include cationic carbocyanines, rhodamines and anionic oxonols, are suitable for detecting changes in a variety of transmembrane potentials of, e.g., nonexcitable cells caused by a variety of biological phenomena, including ion channel permeability. The structures of a variety of available slow response dyes are found e.g., at table 25.3 of Molecular Probes (1996).

Many slow, Nernstian dyes such as carbocyanines, rhodamines and oxonols are used to measure transmembrane potential by virtue of voltage-dependent dye redistribution and fluorescence changes resulting from the redistribution. Fluorescence changes which may be caused by redistribution include: a change of the concentration of the fluorophore within the cell or vesicle, a change in the dye fluorescence due to aggregation or a change in dye fluorescence due to binding to intracellular or intravesicular sites. Typically, 10-15 minutes of equilibration time is used to allow the dyes to redistribute across the cell membrane after changing the transmembrane potential.

Examples of available anionic dyes that can be used for measurement of transmembrane potential include the anionic bis-isoxazolone oxonols which accumulate in the cytoplasm of depolarized cells by a Nernst equilibrium-dependent uptake from the extracellular solution. Of the oxonols studied in one reference ("Kinetics of the Potential-Sensitive Extrinsic Probe Oxonol VI in Beef Heart Submitochondrial Particles." J. C. Smith, B. Chance. *J Membrane Biol* 46, 255 (1979)), oxonol VI gave the largest spectral shifts, with an isosbestic point at 603 nm. Oxonol VI responds to changes in potential more rapidly than oxonol V.

The three common bis-barbituric acid oxonols, often referred to as DiBAC dyes, form a family of spectrally distinct potentiometric probes with excitation maxima at approximately 490 nm ($DiBAC_4(3)$), 530 nm ($DiSBAC_2(3)$) and 590 nm ($DiBAC_4(5)$). $DiBAC_4(3)$ has been used in many publications that cite using a "bis-oxonol" (Molecular Probes, 1999, chapter 23). The dyes enter depolarized cells where they bind to intracellular proteins or membranes and exhibit enhanced fluorescence and red spectral shifts. Increased depolarization results in more influx of the anionic dye and thus an increase in fluorescence. $DiBAC_4(3)$ has particularly high voltage sensitivity. The long-wavelength $DiSBAC_2(3)$ has frequently been used in combination with the UV light-excitable $Ca^{2+}$ indicators indo-1 or fura-2 for the simultaneous measurements of transmembrane potential and $Ca^{2+}$ concentrations (id. at Table 23.2).

Classes of cationic membrane permeable dyes that can be used as ion sensing compositions include, e.g., indo-carbocyanine dyes, thio-carbocyanine dyes, oxa-carbocyanine dyes (see Molecular Probes on-line catalogue, updated as of Aug. 10, 2000, at section 23.3, entitled "Slow-Response Dyes;"http:H/www.probes.com/handbook/sections/2303.html). See also, Sims, et al. (1974) "Studies on the Mechanism by Which Cyanine Dyes Measure Membrane Potential in Red Blood Cells and Phosphatidylcholine Vesicles," *Biochemistry* 13, 3315; Cabrini and Verkman (1986) "Potential-Sensitive Response Mechanism of DiS-C3 (5) in Biological Membranes," *Membrane Biol* 92, 171; Guillet and Kimmich (1981) "DiO-C3-(5) and DiS-C3-(5): Interactions with RBC, Ghosts and Phospholipid Vesicles," *J Membrane Biol* 59, 1; Rottenberg and Wu (1998) "Quantitative Assay by Flow Cytometry of the Mitochondrial Membrane Potential in Intact Cells," *Biochim Biophys Acta* 1404, 393 (1998).

Other useful transmembrane dyes include amino napthylethylenyl pyridinium dyes, and dialkyl amino phenyl polyphenyl pyridinium dyes. The amino napthylethylenyl pyridinium dyes include the ANEP type dyes, e.g., listed in the Molecular Probes catalog (Di-4-ANEPPS, Di-8-ANEPPS, Di-2-ANEPEQ, Di-8-ANEPEQ and Di-12-ANEPEQ). Dialkyl amino phenyl polyphenyl pyridinium dyes include the RH type dyes listed in the Molecular Probes catalog (RH160, RH237, RH 421, RH 704, RH 414, and RH 461).

In general, changes in the level of fluorescence of the biological sample-test compound mixture detected, where the change in fluorescence is indicative of a change in transmembrane potential. Typically, the assay methods described herein are used to detect the effect of the test compound on the transmembrane potential of a cell or other membrane. Where one is seeking to determine the effect of a test compound on a cell's transmembrane potential, e.g., through a change in ion flux, transport, membrane permeability, or the like, one can expose the cell, membrane, etc., to the test compound and the cell etc., is examined for the presence of a previously absent fluorescent signal (or the absence of a previously present fluorescent signal). Of particular interest are the effects of tastant compounds and potential modulators on cellular functioning, as determinable from TMP measurements.

For example, in one assay format, a dye is contacted to a biological sample. In accordance with these methods, the sample can be placed into a reaction vessel, such as a microwell dish, and the level of fluorescence from the composition is measured, optionally over a period of time. This can be used to provide an initial or background level of fluorescence indicative of an existing transmembrane potential for the biological sample. A selected test compound is then added to the biological sample (or these procedures are carried out in parallel, providing control and experimental samples). The test compound can be tested alone, or is added before, together or after addition of a tastants to determine its effect on tastant responses (e.g. enhancement or inhibition). Following the stimulus, the fluorescence level of the biological sample is again measured (typically over time) and compared to the initial fluorescent level or the fluorescence level in a control cell population (e.g., which is exposed to a control TMP modulator). Any change in the level of fluorescence not attributable to dilution by the test compound (as determined from an appropriate control) is then attributable to the effect the test compound has on the cell's transmembrane potential, or rate of TMP change in response to depolarization or hyperpolarization events.

These types of reactions are carried out in an appropriate reaction receptacle that allows measurement of fluorescence, in situ. As such, the receptacle is typically a transparent reaction vessel, such as a test tube, cuvette, a reaction well in a multiwell plate, or a transparent conduit, e.g., a capillary, microchannel or tube.

The assay methods of the present invention are particularly useful in performing high-throughput (greater than 1,000 compounds/day) and even ultra-high throughput (e.g., greater than 10,000 compounds/day) screening of chemical libraries, e.g., in searching for tastant/modulator leads. These experiments may be carried out in parallel by a providing a large number of reaction mixtures (e.g., cell suspensions as described herein) in separate receptacles, typically in a multiwell format, e.g., 96 well, 324 well or 1536 well plates. Different test compounds (library members) are added to separate wells, and the effect of the compound on the reaction mixture is ascertained, e.g., via the fluorescent signal. These parallelized assays are generally carried out using specialized equipment e.g., as described above to enable simultaneous processing of large numbers of samples, i.e., fluid handling by robotic pipettor systems and fluorescent detection by multiplexed fluorescent multi-well plate readers.

Patch Clamping

As noted above, monitoring of transmembrane dye flow is a preferred method of monitoring test compound effects on ion channels. A second preferred method uses voltage clamping, such as patch clamping. This is a particularly useful method e.g., when using *Xenopus* oocytes.

A voltage clamp allows for the measurement of ion currents flowing across a cell membrane. Originally, the voltage clamp used two electrodes and a feedback circuit for transmembrane measurements. In the original Cole-Marmount voltage clamp, both electrodes are placed inside a cell and transmembrane voltage is recorded through one of the electrodes (the "voltage electrode") relative to an outside reference (e.g., ground). The second electrode passes current into the cell and is termed the "current electrode".

Briefly, a "holding voltage" is maintained across the cell membrane. Anytime the cell makes a deviation from this holding voltage by passing an ion current across its membrane, an operational amplifier generates an "error signal". The error signal is the difference between the holding voltage specified by the experimenter and the actual voltage of the cell. The feedback circuit of the voltage clamp passes current into the cell (via the current electrode) in the polarity needed to reduce the error signal to zero. Thus, the current is applied in a polarity opposite current that the cell is passing across its membrane, and the clamp circuit provides a current that is the mirror image of the cellular current. This mirror or "clamp current" can be easily measured, giving an accurate reproduction of the currents flowing across the cell's membrane (although in the opposite polarity).

A modern variant of this general method is the "patch clamp" which uses a single electrode device. The patch clamp technique is in common use to monitor the flow of ions across a membrane (Neher E (1992) "Nobel lecture. Ion channels for communication between and within cells" *Neuron*. 8(4):605-12). The patch clamp technique involves applying a very finely drawn glass micropipette onto the surface of a cell to form an electrode. This electrode is pressed against a cell membrane and suction is applied to the inside of the electrode to pull the cell's membrane inside the tip of the electrode. This suction causes the cell to form a tight seal with the electrode (a "giga-ohm seal," as the electrical resistance of the seal is in excess of one giga-ohm). From this point, at least 4 different experimental approaches can be taken. First, the electrode can be left sealed to a patch of membrane (a "cell-attached patch"). This allows for the recording of currents through single ion channels in that patch of membrane. Second, the electrode can be withdrawn from the cell, ripping a patch of membrane off of the cell. This forms an "inside-out" patch. This is useful when the environment on the inside of an ion channel is to be studied. Third, the electrode can be withdrawn from the cell, allowing a blob of membrane to bud from the cell. When the electrode is pulled away, this blob will part from the cell and reform as a ball of membrane on the end of the electrode, with the outside of the membrane being the surface of the ball (thus the name "outside out patch"). Such "outside out" patching permits examination of the properties of an ion channel when it is protected from the outside environment, but not in contact with it's usual environment. Fourth, the electrode can be left in place, but harder suction is applied to rupture the portion of the cell's membrane that is inside the electrode, providing access to the intracellular space of the cell. This is known as "whole-cell recording". This method is also sometimes misnamed a "whole cell patch." The advantage of whole cell recording is that the sum total current that flows across the cell's membrane can be recorded.

Thus, the voltage clamping such as the patch clamp technique allows the recording of single ion-channel currents, or alternatively currents from entire small cells. In the context of the present invention, this provides a platform for the analysis of changes in currents that result from application of a test compound of modulator.

A modern variant of the classical patch clamp that can be adapted to the present invention is the planar patch clamp, which uses a planar array of PDMS electrodes that mimic a classical glass electrode (Klemic et al. (2002) "Micromolded PDMS Electrode Allows Patch Clamp Electrical Recording From Cells" *Biosensors and Bioelectronics* 597-604). This modern patch clamp is suited to high throughput patch clamp analysis, allowing many different cells to be analyzed for ion channel activity simultaneously.

Additional Screening System Details

Automated systems of the invention can facilitate the screening methods noted above (both in vitro and in vivo screening methods). That is, systems that facilitate cell or biochemical sample based screening for polycystin 2L1/PKD2L1 expression and/or activity are a feature of the invention. Similarly, systems designed to monitor feeding/drinking/licking etc. behavior of animals, including non-human transgenic laboratory animals, are also a feature of the invention. System features herein are generally applicable to the methods herein and vice-versa.

Biological/Biochemical Sources/Libraries

High-throughput automated systems that detect compounds that bind to and/or modulate an activity of a polycystin-2L1 taste receptor polypeptide typically include a biological/biochemical sample (that includes the polycystin-2L1 taste receptor polypeptide, e.g., any cell or other material described herein) and a source of a plurality of test compounds. A detector detects binding of one or more of the test compounds to the polycystin-2L1 taste receptor polypeptide, or modulation of a level or activity of the polypeptide (or mRNA transcript corresponding to the polypeptide) by the test compounds, thereby identifying a putative tastant compound that binds to or modulates the activity of the polycystin-2L1 taste receptor polypeptide.

The source of test compound for such systems and in the practice of the methods of the invention can be any commercially available or proprietary library of materials, including compound libraries from Senomyx (La Jolla, Calif.), Sigma (St. Louis Mo.), Aldrich (St. Louis Mo.), Agilent Technologies (Palo Alto, Calif.) or the like. The format of the library will vary depending on the system to be used. In one typical embodiment, libraries of sample materials are arrayed in microwell plates (e.g., 96, 384 or more well plates), which can be accessed by standard fluid handling robotics, e.g., using a pipettor or other fluid handler with a standard ORCA robot (Optimized Robot for Chemical Analysis) available from Beckman Coulter (Fullerton, Calif.). Standard commercially available workstations such as the Caliper Life Sciences (Hopkinton, Mass.) Sciclone ALH 3000 workstation and Rapidplate™ 96/384 workstation provide precise 96 and 384-well fluid transfers in a small, highly scalable format. Plate management systems such as the Caliper Life Sciences Twister® II Advanced Capability Microplate Handler for End-Users, OEM's and Integrators provide plate handling, storage and management capabilities for fluid handling, while the Presto™ AutoStack provides fast reliable access to consumables presenting trays of tips, reagents, microplates or deep wells to an automated device (e.g., the ALH 3000) without robotic arm intervention.

Microfluidic systems for handling and analyzing microscale fluid samples, including cell based and non-cell based approaches that can be used for analysis of test compounds on biological samples in the present invention are also available, e.g., the Caliper Life Sciences various LabChip® technologies (e.g., LabChip® 90 and 3000) and Agilent Technologies (Palo Alto, Calif.) 2100 and 5100 devices. Similarly, interface devices between microfluidic and standard plate handling technologies are also commercially available. For example, the Caliper Technologies LabChip® 3000 uses "sipper chips" as a "chip-to-world" interface that allows automated sampling from microtiter plates. To meet the needs of high-throughput environments, the LabChip® 3000 employs four or even twelve sippers on a single chip so that samples can be processed, in parallel, up to twelve at a time. Solid phase libraries of materials can also be conveniently accessed using sipper or pipetting technology, e.g., solid phase libraries can be gridded on a surface and dried for later rehydration with a sipper or pipette and accessed through the sipper or pipette.

As already noted, with regard to the systems and methods of the invention, the particular libraries of compounds can be any of those that now exist, e.g., those that are commercially available, or that are proprietary. A number of libraries of test compounds exist, e.g., those from Senomyx (La Jolla, Calif.) (which include libraries pre-screened for desirable tastant properties), Sigma (St. Louis Mo.), and Aldrich (St. Louis Mo.). Other current compound library providers include Actimol (Newark Del.), providing e.g., the Actiprobe 10 and Actiprobe 25 libraries of 10,000 and 25,000 compounds, respectively; BioMol (Philedelphia, Pa.), providing a variety of libraries, including natural compound libraries and the Screen-Well™ Ion Channel ligand library which are usefully screened against the receptors herein, as well as several other application specific libraries; Enamine (Kiev, Ukranie) which produces custom libraries of billions of compounds from thousands of different building blocks, TimTec (Newark Del.), which produces general screening stock compound libraries containing >100,000 compounds, as well as template-based libraries with common heterocyclic lattices, libraries for targeted mechanism based selections, including kinase modulators, GPCR Ligands, channel modulators, etc., privileged structure libraries that include compounds containing chemical motifs that are more frequently associated with higher biological activity than other structures, diversity libraries that include compounds pre-selected from available stocks of compounds with maximum chemical diversity, plant extract libraries, natural products and natural product-derived libraries, etc; AnalytiCon Discovery (Germany) including NatDiverse (natural product analogue screening compounds) and MEGAbolite (natural product screening compounds); Chembridge (San Diego, Calif.) including a wide array of targeted or general and custom or stock libraries; ChemDiv (San Diego, Calif.) providing a variety of compound diversity libraries including CombiLab and the International Diversity Collection; Comgenix (Hungary) including ActiVerse™ libraries; MicroSource (Gaylordsville, Conn.) including natural libraries, agro libraries, the NINDS custom library, the genesis plus library and others; Polyphor (Switzerland) including privileged core structures as well as novel scaffolds; Prestwick Chemical (Washington D.C.), including the Prestwick chemical collection and others that are pre-screened for biotolerance; Tripos (St. Louis, Mo.), including large lead screening libraries; and many others. Academic institutions such as the Zelinsky Institute of Organic Chemistry (Russian Federation) also provide libraries of considerable structural diversity that can be screened in the methods of the invention.

Detectors and other System Components

Although the devices and systems specifically illustrated herein are generally described in terms of the performance of a few or one particular operation, it will be readily appreciated from this disclosure that these systems permit easy integration of additional operations. For example, the systems described will optionally include structures, reagents and systems for performing virtually any number of operations both upstream and downstream from the operations specifically described herein. Such upstream operations include sample handling and preparation operations, e.g., cell separation, extraction, purification, culture, amplification, cellular activation, labeling reactions, dilution, aliquotting, and the like. Similarly, downstream operations may include similar operations, including, e.g., separation of sample components, labeling of components, assays and detection operations, movement of components into contact with cells or other membrane preparations, or materials released from cells or membrane preparations, or the like.

Upstream and downstream assay and detection operations include, without limitation, cell fluorescence assays, cell activity assays, receptor/ligand assays, immunoassays, and the like. Any of these elements can be fixed incorporated into the systems herein.

Instrumentation for high throughput optical screening of cell assays is available. In addition to the systems noted herein, other automated approaches can also be practiced with the dyes and methods of the invention. For example, the FLIPR (Fluorescence Imaging Plate Reader) was developed to perform quantitative optical screening for cell based kinetic assays (Schroder and Neagle (1996) "FLIPR: A New Instrument for Accurate, High Throughput Optical Screening" *Journal of Biomolecular Screening* 1(2):75-80). This device can be adapted to the present invention, e.g., by using dyes to monitor TMP, as discussed above.

In general in the present invention, materials such as cells and dyes are optionally monitored and/or detected so that an activity such as TMP activity can be determined. Depending on the label signal measurements, decisions can be made regarding subsequent operations, e.g., whether to assay a particular tastant/modulator in detail to determine detailed receptor binding/activity kinetic information.

The systems described herein generally include fluid handling devices, as described above, in conjunction with additional instrumentation for controlling fluid transport, flow rate and direction within the devices, detection instrumentation for detecting or sensing results of the operations performed by the system, processors, e.g., computers, for instructing the controlling instrumentation in accordance with preprogrammed instructions, receiving data from the detection instrumentation, and for analyzing, storing and interpreting the data, and providing the data and interpretations in a readily accessible reporting format.

Controllers

A variety of controlling instrumentation is optionally utilized in conjunction with the fluid handling elements described above, for controlling the transport and direction of fluids and/or materials within the systems of the present invention.

Typically, the controller systems are appropriately configured to receive or interface with a fluid handling or other system element as described herein. For example, the controller and/or detector, optionally includes a stage upon which a sample is mounted to facilitate appropriate interfacing between the controller and/or detector and the rest of the system. Typically, the stage includes an appropriate mounting/alignment structural elements, such as a nesting well, alignment pins and/or holes, asymmetric edge structures (e.g., to facilitate proper alignment of microwell plates or microfluidic "chips"), and the like.

Detectors

Within the systems, detectors can take any of a variety of forms. The various fluid handling stations noted above often come with integrated detectors, e.g., optical or fluorescent detectors. However, other detectors such as patch clamp devices, flourescence detectors that detects FRET, changes in membrane potential or flow of a dye into or out of the cell are also suitable, depending on the application.

Generally, devices herein optionally include signal detectors, e.g., which detect fluorescence, phosphorescence, radioactivity, pH, charge, absorbance, luminescence, temperature, magnetism or the like. As noted, fluorescent detection is especially preferred and generally used for detection of voltage sensitive compounds (however, as noted, upstream and downstream operations can be performed on cells, dyes, modulators or the like, which can involve other detection methods).

System signal detectors are typically disposed adjacent to a site of reaction or mixing between the biological/biochemical sample and the test compound. This site can be a test tube, microwell plate, microfluidic device, or the like. The site is within sensory communication of the detector. The phrase "within sensory communication" generally refers to the relative location of the detector that is positioned relative to the site so as to be able to receive a particular relevant signal from that container. In the case of optical detectors, e.g., fluorescence FRET, or fluorescence polarization detectors, sensory communication typically means that the detector is disposed sufficiently proximal to the container that optical, e.g., fluorescent signals, are transmitted to the detector for adequate detection of those signals. Typically this employs a lens, optical train or other detection element, e.g., a CCD, that is focused upon a relevant portion of the container to efficiently gather and record these optical signals.

Example detectors include photo multiplier tubes, spectrophotometers, a CCD array, a scanning detector, a microscope, a galvo-scann or the like. Cells, dyes or other components which emit a detectable signal can be flowed past the detector, or, alternatively, the detector can move relative to an array of samples (or, the detector can simultaneously monitor a number of spatial positions corresponding to samples, e.g., as in a CCD array).

The system typically includes a signal detector located proximal to the site of mixing/reaction. The signal detector detects the detectable signal, e.g., for a selected length of time (t). For example, the detector can include a spectrophotometer, or an optical detection element. Commonly, the signal detector is operably coupled to a computer, which deconvolves the detectable signal to provide an indication of the transmembrane potential, e.g., an indication of a change in the potential over time.

The detector can detect transmembrane potential (the work needed to move a unit of charge across a membrane such as a cell membrane), e.g., through detecting flow of a cationic membrane permeable dye, an anionic Nernstian dye, an anionic membrane permeable dye, or other voltage sensing composition across the membrane over time, e.g., in response to application of a test compound. Changes in the rate of depolarization and hyperpolarization are monitored in response to a test compound, e.g., as compared to a control that does not include the test compound. Premeable dyes are particularly useful for monitoring ion flow, e.g., dyes that can equilibrate across the membrane relatively quickly, typically in about 1 hour, or less. Permeability can be dependent upon the relevant conditions, e.g., temperature, ionic conditions, voltage potentials, or the like.

Computer

As noted above, either or both of the controller system and/or the detection system are coupled to an appropriately programmed processor or computer which functions to instruct the operation of these instruments in accordance with preprogrammed or user input instructions, receive data and information from these instruments, and interpret, manipulate and report this information to the user. As such, the computer is typically appropriately coupled to one or both of these instruments (e.g., including an analog to digital or digital to analog converter as needed).

The computer typically includes appropriate software for receiving user instructions, either in the form of user input into a set parameter fields, e.g., in a GUI, or in the form of preprogrammed instructions, e.g., preprogrammed for a variety of different specific operations. The software then converts these instructions to appropriate language for instructing the operation of the fluid direction and transport controller to carry out the desired operation. The computer then receives the data from the one or more sensors/detectors included within the system, and interprets the data, either provides it in a user understood format, or uses that data to initiate further controller instructions, in accordance with the programming, e.g., such as in monitoring and control of flow rates, temperatures, applied voltages, and the like.

In the present invention, the computer typically includes software for the monitoring of samples. Additionally, the software is optionally used to control flow of materials.

Biosensors

Biosensors of the invention are devices or systems that comprise the polypeptides of the invention (a polycystin 2L1 polypeptide) coupled to a readout that measures or displays one or more activity of the polypeptide. Thus, any of the above described assay components can be configured as a biosensor by operably coupling the appropriate assay components to a readout. The readout can be optical (e.g., to detect cell markers, ion-sensitive dyes, cell potential, or cell survival) electrical (e.g., coupled to a FET, a BIAcore, or any of a variety of others), spectrographic, or the like, and can optionally include a user-viewable display (e.g., a CRT or optical viewing station). The biosensor can be coupled to robotics or other automation, e.g., microfluidic systems, that direct contact of the test compounds to the proteins of the invention, e.g., for automated high-throughput analysis of test compound activity. A large variety of automated systems that can be adapted to use with the biosensors of the invention are commercially available. For example, automated systems have been made to assess a variety of biological phenomena, including, e.g., expression levels of genes in response to selected stimuli (Service (1998) "Microchips Arrays Put DNA on the Spot" *Science* 282:396-399). Laboratory systems can also perform, e.g., repetitive fluid handling operations (e.g., pipetting) for transferring material to or from reagent storage systems that comprise arrays, such as microtiter trays or other chip trays, which are used as basic container elements for a variety of automated laboratory methods. Similarly, the systems manipulate, e.g., microtiter trays and control a variety of environmental conditions such as temperature, exposure to light or air, and the like. Many such automated systems are commercially available. Examples of automated systems are available from Caliper Technologies (including the former Zymark Corporation, Hopkinton, Mass.), which utilize various Zymate systems which typically include, e.g., robotics and fluid handling modules. Similarly, the common ORCA® robot, which is used in a variety of laboratory systems, e.g., for microtiter tray manipulation, is also commercially available, e.g., from Beckman Coulter, Inc. (Fullerton, Calif.). A number of automated approaches to high-throughput activity screening are provided by the Genomics Institute of the Novartis Foundation (La Jolla, Calif.); See GNF.org on the world-wide web. Microfluidic screening applications are also commercially available from Caliper Technologies Corp. For example, (e.g., LabMicrofluidic device® high throughput screening system (HTS) by Caliper Technologies, Mountain View, Calif. or the HP/Agilent technologies Bioanalyzer using LabChip™ technology by Caliper Technologies Corp. can be adapted for use in the present invention.

In an alternate embodiment, conformational changes are detected by coupling the polypeptides of the invention to an electrical readout, e.g., to a chemically coupled field effect transistor (a CHEM-FET) or other appropriate system for detecting changes in conductance or other electrical properties brought about by a conformational shift by the protein of the invention.

Further Details Regarding Methods of Monitoring Polycystin-2L1 Induced Behavior in Animal Models In addition to the various biological and biochemical sample-based screening methods noted herein, the invention also encompasses testing for Polycystin-2L1/PKD2L1 activity in response to test compounds, in vivo. In one embodiment, this is accomplished by introducing a heterologous PKD2L1 taste receptor gene into an animal and expressing an encoded heterologous polycystin-2L1 taste receptor polypeptide in a taste bud of the animal. A putative polycystin-2L1 taste receptor tastant or modulator is provided to the animal, and one or more feeding behavior of the animal is monitored in response to the presence of the putative polycystin-2L1 taste receptor tastant.

Optionally, the animal is a knock-out animal that has a reduced or eliminated function of an endogenous Polycystin-2L1, e.g., in taste bud cells. Knock out animals are useful both for studies of PKD2L1/polycystin-2L1 function (for example, conformation that an animal lacking PKD2L1 is deficient with respect to one or more taste perceptions) and as a target for delivery of a heterologous PKD2L1 gene. That is, in one aspect, the animal is made transgenic with a Polycystin-2L1 gene (a PKD2L1 gene) of interest. For example, a PKD2L1 knock-out mouse that comprises a human transgene for human PKD2L1 will display a response to polycystin 2L1 tastants and modulators similar to a human, providing a good model system for studying response to polycystin-2L1 tastants and modulators. The heterologous gene can be placed under the control of a heterologous promoter that is active in taste bud cells, e.g., a polycystin-2L1 taste receptor gene promoter, a T1R-gene promoter, T2R-gene promoter, TRPM5-gene promoter, a PLCB2 gene promoter, a repeater gene promoter, a gustducin gene promoter, a Gi2 gene promoter, a cytokeratin-19 gene promoter, or another promoter for a gene that is naturally selectively expressed in a taste receptor cell of the tongue or palate epithelium.

Feeding behavior of the animal in response to putative tastants and/or modulators can be monitored by available methods. For example, animals (such as a transgenic PKD2L1 knock out mouse that comprises a human PKD2L1 gene) will lick a device (stick, tube, plate, etc.) coated with a tastant, if the tastant is perceived as pleasurable to the animal. By monitoring increased licking behavior on such devices, the effect of a putative tastant on feeding behavior can be determined. Similarly, a putative tastant can be dissolved in a taste neutral fluid such as water and supplied to the animal (e.g., using a water bottle) to determine if drinking behavior increases, or if the fluid with the putative tastant is drunk preferentially to the neutral fluid. For example, a neutrally flavored "control" can be a water bottle, while a test compound flavored "experimental" bottle can be placed in a control bottle. If the animal (mouse, rabbit, rat, etc.) feeds preferentially on the experimental bottle, then the animal can taste the test compound and perceives the flavor as pleasurable. If the experimental and control bottle are drunk equally, then the animal likely cannot taste the test compound. If the experimental bottle is drunk less than the control, then the animal can likely detect the test compound, and may detect it as being unpleasant. Similar experiments can be performed with a food source flavored with the test compound.

Modulatory activity can be similarly determined. That is, a potential modulator can be administered to the animal (e.g., applied to the taste bud, injected, or supplied in food or drink) and the increase or decrease in feeding/drinking/licking behavior towards a known tastant (e.g., salt or sour) can be detected, essentially as above. If administration of the modulator results in an increase in feeding/drinking/licking behavior towards the known tastant, then the modulator potentiates the response of that taste quality. If feeding/drinking/licking is decreased, then it likely inhibits activity of an attractive taste modality (e.g. sweet), or enhances activity of an aversive taste modality (e.g. bitter). Either activity can be useful, depending on whether an increase in feeding/drinking is desirable (as in certain livestock yield applications or to help prevent hyponatremia by inducing salt consumption), or a decrease in feeding/drinking is desirable (e.g., to treat obesity, metabolic syndrome, high blood pressure, or the like by reducing salt consumption). Examples of modulators include taste receptor agonists, enhancers, antagonists, inverse agonists, etc.

Behavioral Systems

As noted, a further aspect of the invention monitors animal behavior upon application of potential tastants or taste cell modulators. These systems include a non-human animal comprising a heterologous PKD2L1 taste receptor gene that is expressed in a taste bud of the animal and a source of a putative polycystin-2L1 taste receptor tastant that is accessible to the animal. The system further includes a detector that detects a feeding behavior of the animal in response to the presence of the putative polycystin-2L1 taste receptor tastant.

Here again, the animal is typically a knock-out animal (e.g., a mouse) deficient in endogenous polycystin-2L1 taste receptor polypeptide expression, that expresses a heterologous human polycystin-2L1 taste receptor polypeptide. The source can include any of the configurations noted above with respect to the related methods, e.g., a lickable device, a fluid source comprising the tastant, or a food source comprising the tastant.

The detector will typically include a camera or motion sensor that monitors movement of the animal. Alternately, lickable devices can detect pressure against the device through conventional strain measurement devices, or electronically by detecting the completion of a circuit upon licking, or optically by detecting tongue movement. It is also possible to inset electrodes in muscles controlling oromotor activity and monitor their contraction/relaxation as a surrogate for feeding and gagging behavior.

An analysis module, e.g., a computer analyzes information from the detector and can statistically compile information regarding feeding/licking/drinking behavior. The analysis module can include a user viewable display that displays the results of the analysis to a user, e.g., a GUI.

Making Knock-Out Animals and Transgenics

A transgenic animal is simply an animal that has had DNA introduced into one or more of its cells artificially. This is most commonly done in one of two ways. First, DNA can be integrated randomly by injecting it into the pronucleus of a fertilized ovum. In this case, the DNA can integrate anywhere in the genome. In this approach, There is no need for homology between the injected DNA and the host genome. Second, targeted insertion can be accomplished by introducing heterologous DNA into embryonic stem (ES) cells and selecting for cells in which the heterologous DNA has undergone homologous recombination with homologous sequences of the cellular genome. Typically, there are several kilobases of homology between the heterologous and genomic DNA, and positive selectable markers (e.g., antibiotic resistance genes) are included in the heterologous DNA to provide for selection of transformants. In addition, negative selectable markers (e.g., "toxic" genes such as barnase) can be used to select against cells that have incorporated DNA by non-homologous recombination (i.e., random insertion).

One common use of targeted insertion of DNA is to make knock-out mice. Typically, homologous recombination is used to insert a selectable gene driven by a constitutive promoter into an essential exon of the gene that one wishes to disrupt (e.g., the first coding exon). To accomplish this, the selectable marker is flanked by large stretches of DNA that match the genomic sequences surrounding the desired insertion point. Once this construct is electroporated into ES cells, the cells' own machinery performs the homologous recombination. To make it possible to select against ES cells that incorporate DNA by non-homologous recombination, it is common for targeting constructs to include a negatively selectable gene outside the region intended to undergo recombination (typically the gene is cloned adjacent to the shorter of the two regions of genomic homology). Because DNA lying outside the regions of genomic homology is lost during homologous recombination, cells undergoing homologous recombination cannot be selected against, whereas cells undergoing random integration of DNA often can. A commonly used gene for negative selection is the herpes virus thymidine kinase gene, which confers sensitivity to the drug gancyclovir.

Following positive selection and negative selection if desired, ES cell clones are screened for incorporation of the construct into the correct genomic locus. Typically, one designs a targeting construct so that a band normally seen on a Southern blot or following PCR amplification becomes replaced by a band of a predicted size when homologous recombination occurs. Since ES cells are diploid, only one allele is usually altered by the recombination event so, when appropriate targeting has occurred, one usually sees bands representing both wild type and targeted alleles.

The embryonic stem (ES) cells that are used for targeted insertion are derived from the inner cell masses of blastocysts (early mouse embryos). These cells are pluripotent, meaning they can develop into any type of tissue.

Once positive ES clones have been grown up and frozen, the production of transgenic animals can begin. Donor females are mated, blastocysts are harvested, and several ES cells are injected into each blastocyst. Blastocysts are then implanted into a uterine horn of each recipient. By choosing an appropriate donor strain, the detection of chimeric offspring (i.e., those in which some fraction of tissue is derived from the transgenic ES cells) can be as simple as observing hair and/or eye color. If the transgenic ES cells do not contribute to the germline (sperm or eggs), the transgene cannot be passed on to offspring.

Transgenic animals are a useful tool for studying gene function and testing tastants and modulators. Human (or other selected) PKD2L1 genes can be introduced in place of endogenous PKD2L1 genes of a laboratory animal, making it possible to study function of the human (or other) taste receptor in the easily manipulated and studied laboratory animal. It will be appreciated that there is not precise correspondence between receptor function of different animals (humans and mice perceive aspartame differently, for example), making the ability to study the human or other receptor of interest particularly useful. Although similar genetic manipulations can be performed in tissue culture, the interaction of PKD2L1 and polycystin-2L1 in the context of an intact organism provides a more complete and physiologically relevant picture of PKD2L1 and polycystin-2L$^1$ function than could be achieved in simple cell-based screening assays.

Further Details Regarding Cells Comprising PKD2L1/Polycystin-2L1

As already noted, for several embodiments, biological samples to be tested for PKD2L1 expression or polycystin-2L1 expression or concentration are cells or are derived from cell preparations. The cells can be those associated with PKD2L1/polycystin 2L1 expression in vivo, such as taste bud or kidney cells. Alternately, the cells can be derived from a taste bud or kidney cell, e.g., through culture.

However, one feature of the invention is the production of recombinant cells, e.g., expressing a heterologous PKD2L1 gene. In these embodiments, the biological sample to be tested is derived from the recombinant cell, which is selected largely for ease of culture and manipulation. The cells can be, e.g., human, rodent, insect, *Xenopus*, etc. and will typically be a cell in culture (or an oocyte in the case of *Xenopus*).

PKD2L1 nucleic acids are typically introduced into cells in cloning and/or expression vectors to facilitate introduction of the nucleic acid and expression of PKD2L1 to produce polycystin-2L1. Vectors include, e.g., plasmids, cosmids, viruses, YACs, bacteria, poly-lysine, etc. A "vector nucleic acid" is a nucleic acid molecule into which heterologous nucleic acid is optionally inserted which can then be introduced into an appropriate host cell. Vectors preferably have one or more origins of replication, and one or more sites into which the recombinant DNA can be inserted. Vectors often have convenient means by which cells with vectors can be selected from those without, e.g., they encode drug resistance genes. Common vectors include plasmids, viral genomes, and (primarily in yeast and bacteria) artificial chromosomes. "Expression vectors" are vectors that comprise elements that provide for or facilitate transcription of nucleic acids which are cloned into the vectors. Such elements can include, e.g., promoters and/or enhancers operably coupled to a nucleic acid of interest.

In general, appropriate expression vectors are known in the art. For example, pET-14b, pCDNA1Amp, and pVL1392 are available from Novagen and Invitrogen and are suitable vectors for expression in *E. coli*, COS cells and baculovirus infected insect cells, respectively. pcDNA-3, pEAK, and vectors that permit the generation of PKD2L1 RNA for in vitro and in vivo expression experiments (e.g., in vitro translations and *Xenopus* oocyte injections) are also useful. These vectors are illustrative of those that are known in the art. Suitable host cells can be any cell capable of growth in a suitable media and allowing purification of the expressed protein. Examples of suitable host cells include bacterial cells, such as *E. coli, Streptococci, Staphylococci, Streptomyces* and *Bacillus subtilis* cells; fungal cells such as yeast cells, e.g., *Pichia*, and *Aspergillus* cells; insect cells such as *Drosophila* S2 and *Spodoptera* Sf9 cells, mammalian cells such as CHO, COS, and HeLa; and even plant cells.

Cells are transformed with PKD2L1 genes according to standard cloning and transformation methods. Polycystins can also be isolated from resulting recombinant cells using standard methods. General texts which describe molecular biological techniques for making nucleic acids, including the use of vectors, promoters and many other relevant topics, include Berger and Kimmel, *Guide to Molecular Cloning Techniques, Methods in Enzymology* volume 152 Academic Press, Inc., San Diego, Calif. (Berger); Sambrook et al., *Molecular Cloning—A Laboratory Manual* (3nd Ed.), Vol. 1-3, Cold Spring Harbor Laboratory, Cold Spring Harbor, N.Y., 2000 ("Sambrook") and *Current Protocols in Molecular Biology*, F.M. Ausubel et al., eds., Current Protocols, a joint venture between Greene Publishing Associates, Inc. and John Wiley & Sons, Inc., (supplemented through 2002) ("Ausubel")).

In addition, a plethora of kits are commercially available for the preparation, purification and cloning of plasmids or other relevant nucleic acids from cells, (see, e.g., EasyPrep™, FlexiPrep™, both from Pharmacia Biotech; StrataClean™, from Stratagene; and, QIAprep™ from Qiagen). Any isolated and/or purified nucleic acid can be further manipulated to produce other nucleic acids, used to transfect cells, incorporated into related vectors to infect organisms, or the like.

As noted, typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both, (e.g., shuttle vectors) and selection markers for both prokaryotic and eukaryotic systems. Vectors are suitable for replication and integration in prokaryotes, eukaryotes, or both. See, Giliman & Smith, *Gene* 8:81 (1979); Roberts, et al., *Nature*, 328:731 (1987); Schneider, B., et al., *Protein Expr. Purif.* 6435:10 (1995); Ausubel, Sambrook, Berger (above). A catalogue of Bacteria and Bacteriophages useful for cloning is provided, e.g., by the ATCC, e.g., *The ATCC Catalogue of Bacteria and Bacteriophage* published yearly by the ATCC. Additional basic procedures for sequencing, cloning and other aspects of molecular biology and underlying theoretical considerations are also found in Watson et al. (1992) *Recombinant DNA Second Edition, Scientific American Books, NY.*

In addition, essentially any nucleic acid (and virtually any labeled nucleic acid, whether standard or non-standard) can be custom or standard ordered from any of a variety of commercial sources, such as The Midland Certified Reagent Company (mcrc@oligos.com), The Great American Gene Company (www.genco.com), ExpressGen Inc. (www.expressgen.com), Operon Technologies Inc. (Alameda, Calif.) and many others.

Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York); and Atlas and Parks (eds) *The Handbook of Microbiological Media* (1993) CRC Press, Boca Raton, Fla.

Additional Details Regarding Protein Purification and Handling

Purification of polycystin-2L1, can be accomplished using known techniques. Generally, the transformed cells expressing polycystin-2L1 are lysed, crude purification occurs to remove debris and some contaminating proteins, followed by chromatography to further purify the protein to the desired level of purity. Cells can be lysed by known techniques such as homogenization, sonication, detergent lysis and freeze-thaw techniques. Crude purification can occur using ammonium sulfate precipitation, centrifugation or other known techniques. Suitable chromatography includes anion exchange, cation exchange, high performance liquid chromatography (HPLC), gel filtration, affinity chromatography, hydrophobic interaction chromatography, etc. Well known techniques for refolding proteins can be used to obtain the active conformation of the protein when the protein is denatured during intracellular synthesis, isolation or purification.

In general, polycystin 2L1 polypeptides, can be purified, either partially (e.g., achieving a 5×, 10×, 100×, 500×, or 1000× or greater purification), or even substantially to homogeneity (e.g., where the protein is the main component of a solution, typically excluding the solvent (e.g., water or DMSO) and buffer components (e.g., salts and stabilizers) that the polypeptide is suspended in, e.g., if the polypeptide is in a liquid phase), according to standard procedures known to and used by those of skill in the art. Accordingly, polypeptides of the invention can be recovered and purified by any of a number of methods well known in the art, including, e.g., ammonium sulfate or ethanol precipitation, acid or base extraction, column chromatography, affinity column chromatography, anion or cation exchange chromatography, phosphocellulose chromatography, hydrophobic interaction chromatography, hydroxylapatite chromatography, lectin chromatography, gel electrophoresis and the like. Protein refolding steps can be used, as desired, in making correctly folded mature proteins. High performance liquid chromatography (HPLC), affinity chromatography or other suitable methods can be employed in final purification steps where high purity is desired. In one embodiment, antibodies made against polycyctin 2L1 are used as purification reagents, e.g., for affinity-based purification. Once purified, partially or to homogeneity, as desired, the polypeptides are optionally used e.g., as assay components, therapeutic reagents or as immunogens for antibody production.

In addition to other references noted herein, a variety of purification/protein purification methods are well known in the art, including, e.g., those set forth in R. Scopes, *Protein Purification*, Springer-Verlag, N.Y. (1982); Deutscher, *Methods in Enzymology Vol. 182: Guide to Protein Purification*, Academic Press, Inc. N.Y. (1990); Sandana (1997) *Bioseparation of Proteins*, Academic Press, Inc.; Bollag et al. (1996) *Protein Methods*, 2nd Edition Wiley-Liss, NY; Walker (1996) *The Protein Protocols Handbook* Humana Press, NJ; Harris and Angal (1990) *Protein Purification Applications: A Practical Approach* IRL Press at Oxford, Oxford, England; Harris and Angal *Protein Purification Methods: A Practical Approach* IRL Press at Oxford, Oxford, England; Scopes (1993) *Protein Purification: Principles and Practice 3rd Edition* Springer Verlag, N.Y.; Janson and Ryden (1998) *Protein Purification: Principles, High Resolution Methods and Applications, Second Edition* Wiley-VCH, NY; and Walker (1998) *Protein Protocols on CD-ROM* Humana Press, NJ; and the references cited therein.

Those of skill in the art will recognize that, after synthesis, expression and/or purification, proteins can possess a conformation different from the desired conformations of the relevant polypeptides. For example, polypeptides produced by prokaryotic systems often are optimized by exposure to chaotropic agents to achieve proper folding. During purification from, e.g., lysates derived from *E. coli*, the expressed protein is optionally denatured and then renatured. This is accomplished, e.g., by solubilizing the proteins in a chaotropic agent such as guanidine HCl. In general, it is occasionally desirable to denature and reduce expressed polypeptides and then to cause the polypeptides to re-fold into the preferred conformation. For example, guanidine, urea, DTT, DTE, and/or a chaperonin can be added to a translation product of interest. Methods of reducing, denaturing and renaturing proteins are well known to those of skill in the art (see, the references above, and Debinski, et al. (1993) *J. Biol. Chem.*, 268: 14065-14070; Kreitman and Pastan (1993) Bioconjug. Chem.,4: 581-585; and Buchner, et al., (1992) Anal. Biochem., 205:

263-270). Debinski, et al., for example, describe the denaturation and reduction of inclusion body proteins in guanidine-DTE. The proteins can be refolded in a redox buffer containing, e.g., oxidized glutathione and L-arginine. Refolding reagents can be flowed or otherwise moved into contact with the one or more polypeptide or other expression product, or vice-versa.

PKD2L1 nucleic acids optionally comprise a coding sequence fused in-frame to a marker sequence which, e.g., facilitates purification of the encoded polypeptide. Such purification facilitating domains include, but are not limited to, metal chelating peptides such as histidine-tryptophan modules that allow purification on immobilized metals, a sequence which binds glutathione (e.g., GST), a hemagglutinin (HA) tag (corresponding to an epitope derived from the influenza hemagglutinin protein; Wilson, I., et al. (1984) Cell 37:767), maltose binding protein sequences, the FLAG epitope utilized in the FLAGS extension/affinity purification system (Immunex Corp, Seattle, Wash.), and the like. The inclusion of a protease-cleavable polypeptide linker sequence between the purification domain and the sequence of the invention is useful to facilitate purification.

Cell Rescue—Treatement

In one aspect, the invention includes rescue of a cell that is defective in function of one or more endogenous polycystin genes (PKD2L1) or polypeptides (polycystin 2-L1). This can be accomplished simply by introducing a new copy of the gene (or a heterologous nucleic acid that expresses the relevant protein) into a cell. Other approaches, such as homologous recombination to repair the defective gene (e.g., via chimeraplasty) can also be performed. In any event, rescue of function can be measured, e.g., in any of the assays noted herein. Indeed, this can be used as a general method of screening cells in vitro for activity. Accordingly, in vitro rescue of function is useful in this context for the myriad in vitro screening methods noted above, e.g., for the identification of tastants or modulators in cells. The cells that are rescued can include cells in culture, (including primary or secondary cell culture from patients, as well as cultures of well-established cells). Where the cells are isolated from a patient, this has additional diagnostic utility in establishing which sequence is defective in a patient that presents with a tasting defect.

In another aspect, cell rescue occurs in a patient, e.g., a human or veterinary patient, e.g., to remedy a tastant defect. Thus, one aspect of the invention is gene therapy to remedy tasting defects (or even simply to enhance tastant discrimination), in human or veterinary applications. In these applications, the nucleic acids of the invention are optionally cloned into appropriate gene therapy vectors (and/or are simply delivered as naked or liposome-conjugated nucleic acids), which are then delivered (generally topically to the taste buds, but optionally systemically), optionally in combination with appropriate carriers or delivery agents. Proteins can also be delivered directly, but delivery of the nucleic acid is typically preferred in applications where stable expression is desired. For example, in patients that are on a salt restricted diet, administering a more sensitive form of the receptor can be used to reduce salt in the diet.

Vectors for administration typically comprise PKD2L1 genes under the control of a promoter that is expressed in taste bud cells. These can include native PKD2L1 promoters, or other taste bud specific promoters such as a T1R-gene promoter, a T2R-gene promoter, a TRPM5-gene promoter, a PLCB2 gene promoter, a repeater gene promoter, a gustducin gene promoter, a Gi2 gene promoter, a cytokeratin-19 gene promoter, or a promoters for another gene that is naturally selectively expressed in a taste receptor cell of the tongue or palate epithelium.

Compositions for administration, e.g., comprise a therapeutically effective amount of the gene therapy vector or other relevant nucleic acid, and a pharmaceutically acceptable carrier or excipient. Such a carrier or excipient includes, but is not limited to, saline, buffered saline, dextrose, water, glycerol, ethanol, and/or combinations thereof. The formulation is made to suit the mode of administration. In general, methods of administering gene therapy vectors for topical use are well known in the art and can be applied to administration of the nucleic acids of the invention.

Therapeutic compositions comprising one or more nucleic acid of the invention are optionally tested in one or more appropriate in vitro and/or in vivo animal model of disease, to confirm efficacy, tissue metabolism, and to estimate dosages, according to methods well known in the art. In particular, dosages can initially be determined by activity, stability or other suitable measures of the formulation.

Administration is by any of the routes normally used for introducing a molecule into ultimate contact with taste bud cells, though topical administration or direct injection into the taste buds is simplest and therefore preferred. The nucleic acids of the invention are administered in any suitable manner, optionally with one or more pharmaceutically acceptable carriers. Suitable methods of administering such nucleic acids in the context of the present invention to a patient are available, and, although more than one route can be used to administer a particular composition, a particular route can often provide a more immediate and more effective action or reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention. Compositions can be administered by a number of routes including, but not limited to: oral (in this case, topical and oral can be the same or different, e.g., topical delivery to the taste buds can be oral, as can systemic administration by the GI tract), intravenous, intraperitoneal, intramuscular, transdermal, subcutaneous, topical, sublingual, or rectal administration. Compositions can be administered via liposomes (e.g., topically), or via topical delivery of naked DNA or viral vectors. Such administration routes and appropriate formulations are generally known to those of skill in the art.

The compositions, alone or in combination with other suitable components, can also be made into aerosol formulations (i.e., they can be "nebulized") to be administered via inhalation. Aerosol formulations can be placed into pressurized acceptable propellants, such as dichlorodifluoromethane, propane, nitrogen, and the like. Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations of packaged nucleic acid can be presented in unit-dose or multi-dose sealed containers, such as ampules and vials.

The dose administered to a patient, in the context of the present invention, is sufficient to effect a beneficial therapeutic response in the patient over time, or, e.g., to provide sweet or glutamate tastant discrimination as perceived by the patient in an objective sweet or glutamate tastant test. The dose is determined by the efficacy of the particular vector, or other formulation, and the activity, stability or serum half-life of the polypeptide which is expressed, and the condition of the patient, as well as the body weight or surface area of the patient to be treated. The size of the dose is also determined by the existence, nature, and extent of any adverse side-effects that accompany the administration of a particular vector, formulation, or the like in a particular patient. In determining the effective amount of the vector or formulation to be administered in the treatment of disease, the physician evaluates local expression in the taste buds, or circulating plasma levels, formulation toxicities, progression of the relevant disease, and/or where relevant, the production of antibodies to proteins encoded by the polynucleotides. The dose administered, e.g., to a 70 kilogram patient are typically in the range equivalent to dosages of currently-used therapeutic proteins, adjusted for the altered activity or serum half-life of the relevant composition. The vectors of this invention can supplement treatment conditions by any known conventional therapy (e.g., diet restriction, etc.).

For administration, formulations of the present invention are administered at a rate determined by the LD-50 of the relevant formulation, and/or observation of any side-effects of the vectors of the invention at various concentrations, e.g., as applied to the mass or topical delivery area and overall health of the patient. Administration can be accomplished via single or divided doses.

If a patient undergoing treatment develops fevers, chills, or muscle aches, he/she receives the appropriate dose of aspirin, ibuprofen, acetaminophen or other pain/fever controlling drug. Patients who experience reactions to the compositions, such as fever, muscle aches, and chills are premedicated 30 minutes prior to the future infusions with either aspirin, acetaminophen, or, e.g., diphenhydramine. Meperidine is used for more severe chills and muscle aches that do not quickly respond to antipyretics and antihistamines. Treatment is slowed or discontinued depending upon the severity of the reaction.

Detecting Polymorphisms

In one aspect, the invention includes detecting a polymorphism in a PKD2L1 gene (or a nucleic acid in linkage disequilibrium with such a polymorphism) to detect a taste receptor abnormality. A "polymorphism" is a locus that is variable; that is, within a population, the nucleotide sequence at a polymorphism has more than one version or allele. The term "allele" refers to one of two or more different nucleotide sequences that occur or are encoded at a specific locus, or two or more different polypeptide sequences encoded by such a locus. For example, a first allele can occur on one chromosome, while a second allele occurs on a second homologous chromosome, e.g., as occurs for different chromosomes of a heterozygous individual, or between different homozygous or heterozygous individuals in a population. One example of a polymorphism is a "single nucleotide polymorphism" (SNP), which is a polymorphism at a single nucleotide position in a genome (the nucleotide at the specified position varies between individuals or populations). An allele "positively" correlates with a trait when it is linked to it and when presence of the allele is an indictor that the trait or trait form will occur in an individual comprising the allele. An allele negatively correlates with a trait when it is linked to it and when presence of the allele is an indicator that a trait or trait form will not occur in an individual comprising the allele.

In the present case, the gene for tastant defects is identified (PKD2L1). Polymorphisms within or linked to (in linkage disequilibrium with) the gene likely correlate to altered taste perception. Thus, tastant defects or abnormalities can be detected by detecting polymorphisms in the gene.

In general, markers corresponding to polymorphisms between members of a population can be detected by numerous methods well-established in the art (e.g., PCR-based sequence specific amplification, restriction fragment length polymorphisms (RFLPs), isozyme markers, northern analysis, allele specific hybridization (ASH), array based hybridization, amplified variable sequences of the genome, self-sustained sequence replication, simple sequence repeat (SSR), single nucleotide polymorphism (SNP), random amplified polymorphic DNA ("RAPD") or amplified fragment length polymorphisms (AFLP). In one additional embodiment, the presence or absence of a molecular marker is determined simply through nucleotide sequencing of the polymorphic marker region. Any of these methods are readily adapted to high throughput analysis.

Additional Details Regarding Sequence Variations

A number of particular polycystin 2L1 polypeptides and coding nucleic acids are described herein by sequence (See, e.g., the Examples section below). These polycystin 2L1 polypeptides and coding nucleic acids can be modified, e.g., by mutation as described herein, or simply by artificial synthesis of a desired variant. Several types of example variants are described below.

Splice Variants

Given the significant number of exons found in PKD2L1, the presence of splice variants in taste receptor cells is likely. These can be expressed alone or in combination and can be detected or monitored by analysis of taste cell mRNA using PKD2L1 exon-specific primers and the polymerase chain reaction.

Silent Variations

Due to the degeneracy of the genetic code, any of a variety of nucleic acids sequences encoding polypeptides of the invention are optionally produced, some which can bear lower levels of sequence identity to the PKD2L1 nucleic acids in the Examples below. The following provides a typical codon table specifying the genetic code, found in many biology and biochemistry texts.

TABLE 1

Codon Table

| Amino acids | | | Codon |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |

TABLE 1-continued

Codon Table

| Amino acids | | | Codon |
|---|---|---|---|
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

The codon table shows that many amino acids are encoded by more than one codon. For example, the codons AGA, AGG, CGA, CGC, CGG, and CGU all encode the amino acid arginine. Thus, at every position in the nucleic acids of the invention where an arginine is specified by a codon, the codon can be altered to any of the corresponding codons described above without altering the encoded polypeptide. It is understood that U in an RNA sequence corresponds to T in a DNA sequence.

Such "silent variations" are one species of "conservatively modified variations", discussed below. One of skill will recognize that each codon in a nucleic acid (except ATG, which is ordinarily the only codon for methionine) can be modified by standard techniques to encode a functionally identical polypeptide. Accordingly, each silent variation of a nucleic acid which encodes a polypeptide is implicit in any described sequence. The invention, therefore, explicitly provides each and every possible variation of a nucleic acid sequence encoding a polypeptide of the invention that could be made by selecting combinations based on possible codon choices. These combinations are made in accordance with the standard triplet genetic code (e.g., as set forth in Table 1, or as is commonly available in the art) as applied to the nucleic acid sequence encoding a polycystin polypeptide of the invention. All such variations of every nucleic acid herein are specifically provided and described by consideration of the sequence in combination with the genetic code. One of skill is fully able to make these silent substitutions using the methods herein.

Conservative Variations

"Conservatively modified variations" or, simply, "conservative variations" of a particular nucleic acid sequence or polypeptide are those which encode identical or essentially identical amino acid sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

Conservative substitution tables providing functionally similar amino acids are well known in the art. Table 2 sets forth six groups which contain amino acids that are "conservative substitutions" for one another.

TABLE 2

Conservative Substitution Groups

| 1 | Alanine (A) | Serine (S) | Threonine (T) | |
|---|---|---|---|---|
| 2 | Aspartic acid (D) | Glutamic acid (E) | | |
| 3 | Asparagine (N) | Glutamine (Q) | | |
| 4 | Arginine (R) | Lysine (K) | | |
| 5 | Isoleucine (I) | Leucine (L) | Methionine (M) | Valine (V) |
| 6 | Phenylalanine (F) | Tyrosine (Y) | Tryptophan (W) | |

Thus, "conservatively substituted variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group.

Finally, the addition or deletion of sequences which do not alter the encoded activity of a nucleic acid molecule, such as the addition or deletion of a non-functional sequence, is a conservative variation of the basic nucleic acid or polypeptide.

One of skill will appreciate that many conservative variations of the nucleic acid constructs which are disclosed yield a functionally identical construct. For example, as discussed above, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

Antibodies

In another aspect, antibodies to polycystin 2L1 polypeptides can be generated using methods that are well known. The antibodies can be utilized for detecting and/or purifying polycystin 2L1 polypeptides e.g., in situ to monitor localization of receptor, or simply in a biological sample of interest. Antibodies can optionally discriminate the polycystin 2L1 polypeptides from various polycystin homologues, and/or can be used in biosensor applications. As used herein, the term "antibody" includes, but is not limited to, polyclonal antibodies, monoclonal antibodies, humanized or chimeric antibodies and biologically functional antibody fragments, which are those fragments sufficient for binding of the antibody fragment to the protein.

For the production of antibodies to a polycystin 2L1 polypeptide encoded by one of the disclosed sequences or conservative variant or fragment thereof, various host animals may be immunized by injection with the polypeptide, or a portion thereof. Such host animals may include, but are not limited to, rabbits, mice and rats, to name but a few. Various adjuvants may be used to enhance the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (*bacille Calmette-Guerin*) and *Corynebacterium parvum*.

Polyclonal antibodies are heterogeneous populations of antibody molecules derived from the sera of animals immunized with an antigen, such as target gene product, or an antigenic functional derivative thereof. For the production of polyclonal antibodies, host animals, such as those described above, may be immunized by injection with the encoded protein, or a portion thereof, supplemented with adjuvants as also described above.

Monoclonal antibodies (mAbs), which are homogeneous populations of antibodies to a particular antigen, may be obtained by any technique which provides for the production of antibody molecules by continuous cell lines in culture. These include, but are not limited to, the hybridoma technique of Kohler and Milstein (*Nature* 256:495-497, 1975; and U.S. Pat. No. 4,376,110), the human B-cell hybridoma technique (Kosbor et al., *Immunology Today* 4:72, 1983; Cole et al., *Proc. Nat'l. Acad. Sci. USA* 80:2026-2030, 1983), and the EBV-hybridoma technique (Cole et al., *Monoclonal Antibodies and Cancer Therapy*, Alan R. Liss, Inc., pp. 77-96, 1985). Such antibodies may be of any immunoglobulin class, including IgG, IgM, IgE, IgA, IgD, and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., *Proc. Nat'l. Acad. Sci. USA* 81:6851-6855, 1984; Neuberger et al., *Nature* 312:604-608, 1984; Takeda et al., *Nature* 314:452-454, 1985) by splicing the genes from a mouse antibody molecule of appropriate antigen specificity, together with genes from a human antibody molecule of appropriate biological activity, can be used. A chimeric antibody is a molecule in which different portions are derived from different animal species, such as those having a-variable or hypervariable region derived from a murine mAb and a human immunoglobulin constant region.

Alternatively, techniques described for the production of single-chain antibodies (U.S. Pat. No. 4,946,778; Bird, *Science* 242:423-426, 1988; Huston et al., *Proc. Nat'l. Acad. Sci. USA* 85:5879-5883, 1988; and Ward et al., *Nature* 334:544-546, 1989) can be adapted to produce differentially expressed gene-single chain antibodies. Single chain antibodies are formed by linking the heavy and light chain fragments of the Fv region via an amino acid bridge, resulting in a single-chain polypeptide.

In one aspect, techniques useful for the production of "humanized antibodies" can be adapted to produce antibodies to the proteins, fragments or derivatives thereof. Such techniques are disclosed in U.S. Pat. Nos. 5,932,448; 5,693,762; 5,693,761; 5,585,089; 5,530,101; 5,569,825; 5,625,126; 5,633,425; 5,789,650; 5,661,016; and 5,770,429.

Antibody fragments which recognize specific epitopes may be generated by known techniques. For example, such fragments include, but are not limited to, the $F(ab')_2$ fragments, which can be produced by pepsin digestion of the antibody molecule, and the Fab fragments, which can be generated by reducing the disulfide bridges of the $F(ab')_2$ fragments. Alternatively, Fab expression libraries may be constructed (Huse et al., Science 246:1275-1281, 1989) to allow rapid and easy identification of monoclonal Fab fragments with the desired specificity.

The protocols for detecting and measuring the expression of the described polycystin 2L1 polypeptides herein, using the above mentioned antibodies, are well known in the art. Such methods include, but are not limited to, dot blotting, western blotting, competitive and noncompetitive protein binding assays, enzyme-linked immunosorbant assays (ELISA), immunohistochemistry, fluorescence-activated cell sorting (FACS), and others commonly used and widely described in scientific and patent literature, and many employed commercially.

One method, for ease of detection, is the sandwich ELISA, of which a number of variations exist, all of which are intended to be encompassed by the present invention. For example, in a typical forward assay, unlabeled antibody is immobilized on a solid substrate and the sample to be tested is brought into contact with the bound molecule and incubated for a period of time sufficient to allow formation of an antibody-antigen binary complex. At this point, a second antibody, labeled with a reporter molecule capable of inducing a detectable signal, is then added and incubated, allowing time sufficient for the formation of a ternary complex of antibody-antigen-labeled antibody. Any unreacted material is washed away, and the presence of the antigen is determined by observation of a signal, or may be quantitated by comparing with a control sample containing known amounts of antigen. Variations on the forward assay include the simultaneous assay, in which both sample and antibody are added simultaneously to the bound antibody, or a reverse assay, in which the labeled antibody and sample to be tested are first combined, incubated and added to the unlabeled surface bound antibody. These techniques are well known to those skilled in the art, and the possibility of minor variations will be readily apparent. As used herein, "sandwich assay" is intended to encompass all variations on the basic two-site technique. For the immunoassays of the present invention, the only limiting factor is that the labeled antibody be an antibody which is specific for the protein expressed by the gene of interest.

The most commonly used reporter molecules in this type of assay are either enzymes, fluorophore- or radionuclide-containing molecules. In the case of an enzyme immunoassay, an enzyme is conjugated to the second antibody, usually by means of glutaraldehyde or periodate. As will be readily recognized, however, a wide variety of different ligation techniques exist which are well-known to the skilled artisan. Commonly used enzymes include horseradish peroxidase, glucose oxidase, beta-galactosidase and alkaline phosphatase, among others. The substrates to be used with the specific enzymes are generally chosen for the production, upon hydrolysis by the corresponding enzyme, of a detectable color change. For example, p-nitrophenyl phosphate is suitable for use with alkaline phosphatase conjugates; for peroxidase conjugates, 1,2-phenylenediamine or toluidine are commonly used. It is also possible to employ fluorogenic substrates, which yield a fluorescent product, rather than the chromogenic substrates noted above. A solution containing the appropriate substrate is then added to the tertiary complex. The substrate reacts with the enzyme linked to the second antibody, giving a qualitative visual signal, which may be further quantitated, usually spectrophotometrically, to give an evaluation of the amount of PLAB which is present in the serum sample.

Alternately, fluorescent compounds, such as fluorescein and rhodamine, can be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic longer wavelength. The emission appears as a characteristic color visually detectable with a light microscope. Immunofluorescence and EIA techniques are both very well established in the art and are particularly preferred for the present method. However, other reporter molecules, such as radioisotopes, chemiluminescent or bioluminescent molecules may also be employed. It will be readily apparent to the skilled artisan how to vary the procedure to suit the required use.

Further Details Regarding Polycystin Variants

Any of a variety of polycystin 2L1 polypeptides and coding PKD2L1 nucleic acids can be used in the present invention. These include human polycystin-2L1 taste receptor polypeptides and coding PKD2L1 genes, murine polycystin-2L1 taste receptor polypeptides and coding PKD2L1 genes, and polypeptides and coding nucleic acids from a domesticated or livestock animal. Examples of such polypeptides and coding PKD2L1 genes are available, including polycystin-2L1 and PKD2L1 for mice, humans and dogs. Examples of such sequences are provided in the Examples section below and are further available in public databases.

The sequence of any available PKD2L1 gene and coded polypeptide can be modified by standard methods to provide variants of such available sequences, including conservative or non-conservative variants. Any available mutagenesis procedure can be used to modify a PKD2L1 gene. Such mutagenesis procedures optionally include selection of mutant nucleic acids and polypeptides for one or more activity of interest (e.g., increased responsiveness to tastant stimuli, which can be useful in producing transgenic animals, or for biosensor applications). Procedures that can be used include, but are not limited to: site-directed point mutatgenesis, random point mutagenesis, in vitro or in vivo homologous recombination (DNA shuffling), mutagenesis using uracil containing templates, oligonucleotide-directed mutagenesis, phosphorothioate-modified DNA mutagenesis, mutagenesis using gapped duplex DNA, point mismatch repair, mutagenesis using repair-deficient host strains, restriction-selection and restriction-purification, deletion mutagenesis, mutagenesis by total gene synthesis, double-strand break repair, and many others known to persons of skill. Mutagenesis, e.g., involving chimeric constructs, are also included in the present invention. In one embodiment, mutagenesis can be guided by known information of the naturally occurring molecule or altered or mutated naturally occurring molecule, e.g., sequence, sequence comparisons, physical properties, crystal structure or the like. In another class of embodiments, modification is essentially random (e.g., as in classical DNA shuffling).

Additional information regarding mutation is found in the following publications and references cited within: Arnold, *Protein engineering for unusual environments, Current Opinion in Biotechnology* 4:450-455 (1993); Bass et al., *Mutant Trp repressors with new DNA-binding specificities, Science* 242:240-245 (1988); Botstein & Shortle, *Strategies and applications of in vitro mutagenesis, Science* 229:1193-1201 (1985); Carter et al., *Improved oligonucleotide site-directed mutagenesis using M13 vectors, Nucl. Acids Res.* 13: 4431-4443 (1985); Carter, *Site-directed mutagenesis, Biochem. J.* 237:1-7 (1986); Carter, *Improved oligonucleotide-directed mutagenesis using M13 vectors, Methods in Enzymol.* 154: 382-403 (1987); Dale et al., *Oligonucleotide-directed random mutagenesis using the phosphorothioate method, Methods Mol. Biol.* 57:369-374 (1996); Eghtedarzadeh & Henikoff, *Use of oligonucleotides to generate large deletions, Nucl. Acids Res.* 14: 5115 (1986); Fritz et al., *Oligonucleotide-directed construction of mutations: a gapped duplex DNA procedure without enzymatic reactions in vitro, Nucl. Acids Res.* 16: 6987-6999 (1988); Grundström et al., *Oligonucleotide-directed mutagenesis by microscale 'shot-gun' gene synthesis, Nucl. Acids Res.* 13: 3305-3316 (1985); Kunkel, *The efficiency of oligonucleotide directed mutagenesis*, in *Nucleic Acids & Molecular Biology* (Eckstein, F. and Lilley, D. M. J. eds., Springer Verlag, Berlin)) (1987); Kunkel, *Rapid and efficient site-specific mutagenesis without phenotypic selection, Proc. Natl. Acad. Sci. USA* 82:488-492 (1985); Kunkel et al., *Rapid and efficient site-specific mutagenesis without phenotypic selection, Methods in Enzymol.* 154, 367-382 (1987); Kramer et al., *The gapped duplex DNA approach to oligonucleotide-directed mutation construction, Nucl. Acids Res.* 12: 9441-9456 (1984); Kramer & Fritz *Oligonucleotide-directed construction of mutations via gapped duplex DNA, Methods in Enzymol.* 154:350-367 (1987); Kramer et al., *Point Mismatch Repair, Cell* 38:879-887 (1984); Kramer et al., *Improved enzymatic in vitro reactions in the gapped duplex DNA approach to oligonucleotide-directed construction of mutations, Nucl. Acids Res.* 16: 7207 (1988); Ling et al., *Approaches to DNA mutagenesis: an overview, Anal Biochem.* 254(2): 157-178 (1997); Lorimer and Pastan *Nucleic Acids Res.* 23, 3067-8 (1995); Mandecki, *Oligonucleotide-directed double-strand break repair in plasmids of Escherichia coli: a method for site-specific mutagenesis, Proc. Natl. Acad. Sci. USA,* 83:7177-7181 (1986); Nakamaye & Eckstein, *Inhibition of restriction endonuclease Nci I cleavage by phosphorothioate groups and its application to oligonucleotide-directed mutagenesis, Nucl. Acids Res.* 14: 9679-9698 (1986); Nambiar et al., *Total synthesis and cloning of a gene coding for the ribonuclease S protein, Science* 223: 1299-1301 (1984); Sakamar and Khorana, *Total synthesis and expression of a gene for the a-subunit of bovine rod outer segment guanine nucleotide-binding protein (transducin), Nucl. Acids Res.* 14: 6361-6372 (1988); Sayers et al., *Y-T Exonucleases in phosphorothioate-based oligonucleotide-directed mutagenesis, Nucl. Acids Res.* 16:791-802 (1988); Sayers et al., *Strand specific cleavage of phosphorothioate-containing DNA by reaction with restriction endonucleases in the presence of ethidium bromide*, (1988) *Nucl. Acids Res.* 16: 803-814; Sieber, et al., *Nature Biotechnology*, 19:456-460 (2001); Smith, *In vitro mutagenesis, Ann. Rev. Genet.* 19:423-462(1985); *Methods in Enzymol.* 100: 468-500 (1983); *Methods in Enzymol.* 154: 329-350 (1987); Stemmer, *Nature* 370, 389-91 (1994); Taylor et al., *The use of phosphorothioate-modified DNA in restriction enzyme reactions to prepare nicked DNA, Nucl. Acids Res.* 13: 8749-8764 (1985); Taylor et al., *The rapid generation of oligonucleotide-directed mutations at high frequency using phosphorothioate-modified DNA, Nucl. Acids Res.* 13: 8765-8787 (1985); Wells et al., *Importance of hydrogen-bond formation in stabilizing the transition state of subtilisin, Phil. Trans. R. Soc. Lond.* A 317: 415-423 (1986); Wells et al., *Cassette mutagenesis: an efficient method for generation of multiple mutations at defined sites, Gene* 34:315-323 (1985); Zoller & Smith, *Oligonucleotide-directed mutagenesis using M13-derived vectors: an efficient and general procedure for the production of point mutations in any DNA fragment, Nucleic Acids Res.* 10:6487-6500 (1982); Zoller & Smith, *Oligonucleotide-directed mutagenesis of DNA fragments cloned into M13 vectors,* Methods in Enzymol. 100:468-500 (1983); and Zoller & Smith, *Oligonucleotide-directed mutagenesis: a simple method using two oligonucleotide primers and a single-stranded DNA template, Methods in Enzymol.* 154:329-350 (1987). Additional details on many of the above methods can be found in *Methods in Enzymology* Volume 154, which also describes useful controls for trouble-shooting problems with various mutagenesis methods.

Kits

In an additional aspect, the present invention provides kits embodying the methods, composition, systems or apparatus herein. Kits of the invention optionally comprise one or more of the following: (1) a composition, system, system component as described herein; (2) instructions for practicing the methods described herein, and/or for using the compositions or operating the system or system components herein; (3) one or more polycystin 2L1 polypeptide or PKD2L1 nucleic acid; (4) a container for holding components or compositions, and, (5) packaging materials.

EXAMPLES

The following Examples serve to illustrate, but not to limit the invention. One of skill will recognize a variety of non-critical parameters that can be changed to achieve essentially similar results.

A Novel Ion Channel Preferentially Expressed in Mammalian Taste Receptor Cells

Introduction

Taste transduction is one of the most sophisticated forms of chemotransduction in animals (Avenet & Lindemann (1989) Perspectives in taste reception. 112, 1-8; Margolskee (1993) R. Bioessays 15, 645-650). Gustatory signaling is found throughout the animal kingdom, from simple metazoans to the most complex of vertebrates; its main purpose is to provide a reliable signaling response to non-volatile ligands. Mammals are believed to have five basic types of taste modalities: salty, sour, sweet, umami (the taste of MSG), and bitter. Each of these is thought to be mediated by distinct signaling pathways leading to receptor cell depolarization, generation of a receptor or action potential, and release of neurotransmitter and synaptic activity (Roper (1989) *Ann. Rev. Neurosci.* 12:329-353). Recently, the receptors for bitter, sweet and umami were cloned and shown to be encoded by two families of G-protein coupled receptors (Nelson et al. (2001) "Mammalian sweet taste receptors" *Cell* 106(3): 381-90; Nelson et al. (2002) "An amino-acid taste receptor" *Nature* 416(6877): 199-202; Zhang et al. (2003) "Coding of sweet, bitter, and umami tastes: different receptor cells sharing similar signaling pathways" *Cell*, 112(3):293-301; Zhao et al. (2003) "The receptors for mammalian sweet and umami taste" *Cell* 115(3):255-66; Mueller et al. (2005) "The receptors and coding logic for bitter taste" *Nature* 434 (7030): 225-9. In contrast, most of the molecular components of sour or salty pathways remain unknown. Electrophysiological studies suggest that sour and salty tastants modulate taste cell function by direct entry of H+ and Na+ ions through specialized membrane channels on the apical surface of the cell. Thus, ion channels selectively expressed in taste receptor cells are ideal candidates as mediators of salt and sour tastes. Alternatively, ion channels may function as the final critical signaling component in the activation of taste cells (akin to the role of TRPM5 in sweet, umami and bitter cells; Zhang et al. (2003) "Coding of sweet, bitter, and umami tastes: different receptor cells sharing similar signaling pathways" *Cell* 112(3):293-30).

The identification and isolation of taste signaling molecules, in particular receptors, ion channels and signaling components, would allow for pharmacological and genetic modulation of taste signaling pathways. For example, availability of receptor and channel molecules (which are accessible from outside of the cell) would permit the screening for high affinity agonists, antagonists, inverse agonists, and enhancers of taste cell activity. These could then be used in the pharmaceutical and food industry to custom tune, enhance, block, or modulate different tastes. In addition, these cDNAs serve as invaluable tools in the generation of taste (tongue-brain) topographic maps of sensory coding, and the dissection of taste-induced behaviors. Here we report the cloning and characterization of a taste-specific ion channel.

Overview

To discover novel receptors, ion channels and other membrane signaling molecules involved in signal transduction in taste receptor cells, we developed a novel bioinformatics/molecular screening strategy. Our approach relied on two empirical assumptions: First, receptors and ion channels are transmembrane proteins. Second, sensory receptors in the visual, olfactory, touch and taste systems are often selectively expressed in restricted numbers of tissues. Therefore, we searched the mouse genome for transmembrane proteins, and then screened for those with restricted expression. Chosen molecules were subjected to experimental validation by PCR amplification reactions using taste tissue and in situ hybridization studies against mouse tongues.

Using a Hidden Markov Model (TMHMM 2.0) and f_TM-HMM (UCSD Supercomputing Center, Bourne lab), we screened the entire Ensembl mouse genome database for genes encoding putative transmembrane domains. In order to determine the tissue distribution for the chosen candidate genes, we used mouse Expression Sequence Tag (EST) databases (www.ncbi.nlm.nih.gov/BLAST) to identify gene transcripts (i.e., cDNAs) expressed in 3 tissues/organs or less. PCR amplification primers were then prepared against selected cDNAs and RT-PCR reactions using mRNA from taste and non-taste tissues were carried out. Candidates preferentially expressed in taste receptor cells were used for RNA in situ hybridization against various taste papillae. This strategy led to the isolation of a novel taste-specific ion channel.

Bioinformatics Screen

Using a Hidden Markov Model (TMHMM 2.0) and f_TM-HMM (UCSD Supercomputing Center, Bourne lab) we screened the entire Ensembl mouse genome database for genes encoding transmembrane domains. In order to determine the tissue distribution for candidate cDNAs encoding transmembrane proteins, we used mouse Expression Sequence Tag (EST) databases as an expression filter (www.ncbi.nlm.nih.gov/BLAST); each cDNA expressed in 3 tissues/organs or less, was chosen for further study.

Summary of results: (1) We identified ~10,000 predicted and annotated transcripts encoding candidate transmembrane domains (Ensembl version mm.30). (2) 1138 genes were selected by EST analyses as being expressed in 3 tissues or less. (3) 659 genes were subjected to taste versus non-taste RT-PCR reactions using primers against the last exon and/or the 3' untranslated region (primers were designed using http://frodo.wi.mit.edu/cgi-bin/primer3/primer3_www.cgi). (4) 143 candidates were chosen for in situ analysis Tissue Collection & RT-PCR Screen:

In order to determine if candidate cDNAs were selectively expressed in taste receptor cells—a primary goal of this example—we performed RT-PCR reactions using mRNA from taste and non-taste tissue.

Peeled, hand-dissected circumvallate and foliate taste papillae from ~20 mice were collected for each mRNA extraction (total of ~120 mice were used). Tissue was stored in RNAlater (Qiagen), and mRNA was extracted using Micro-FastTrack 2.0 mRNA extraction kit (Invitrogen). cDNA was synthesized using SuperScript II first-strand cDNA synthesis kit (Invitrogen) using oligo(dT) as primers. cDNA synthesis and progress was monitored by using T1R3 (Nelson et al., 2001) and GAPDH as controls.

RT-PCR experiments were performed using a minimum of two independent RT preparations, each containing a mix of circumvallate and folliate mRNA (taste mRNA). As counter-screen, we sampled each candidate cDNA in two independent RT reactions using tongue epithelium devoid of taste receptor cells (non-taste mRNA). 143 of the 659 candidates showed specific RT-PCR reaction products in taste samples but not in any of the non-taste reactions.

Data-Mining & RNA in situ Hybridization:

Candidates shown to be selectively enriched in taste tissue by RT-PCR were examined in detail using BLAST (http://www.ncbi.nlm.nih.gov/BLAST/) and motif search engines, and subjected to RNA in situ hybridizations experiments (see methods section in Hoon et al. (1999) "Putative mammalian taste receptors: a class of taste-specific GPCRs with distinct topographic selectivity" Cell 96:541-51 for details on in situ preparations). Male and female mouse tongues containing different taste papillae were used in all in situ studies. Clone ID 529-30/597-8 was shown to be expressed in selective subsets of taste receptor cells. FIG. 1 shows results from the RNA in situ hybridization in circumvallate taste papillae. Note the expression in subsets of taste cells, but not in surrounding non-taste tissue.

Clone ID529-30/597-8:

This gene was (a) isolated as one of the candidates of the bioinformatics screen, (b) found to be enriched in taste papillae using our RT-PCR screen, and (c) shown to be expressed in a selective subset of taste receptor cells.

Figure 2:
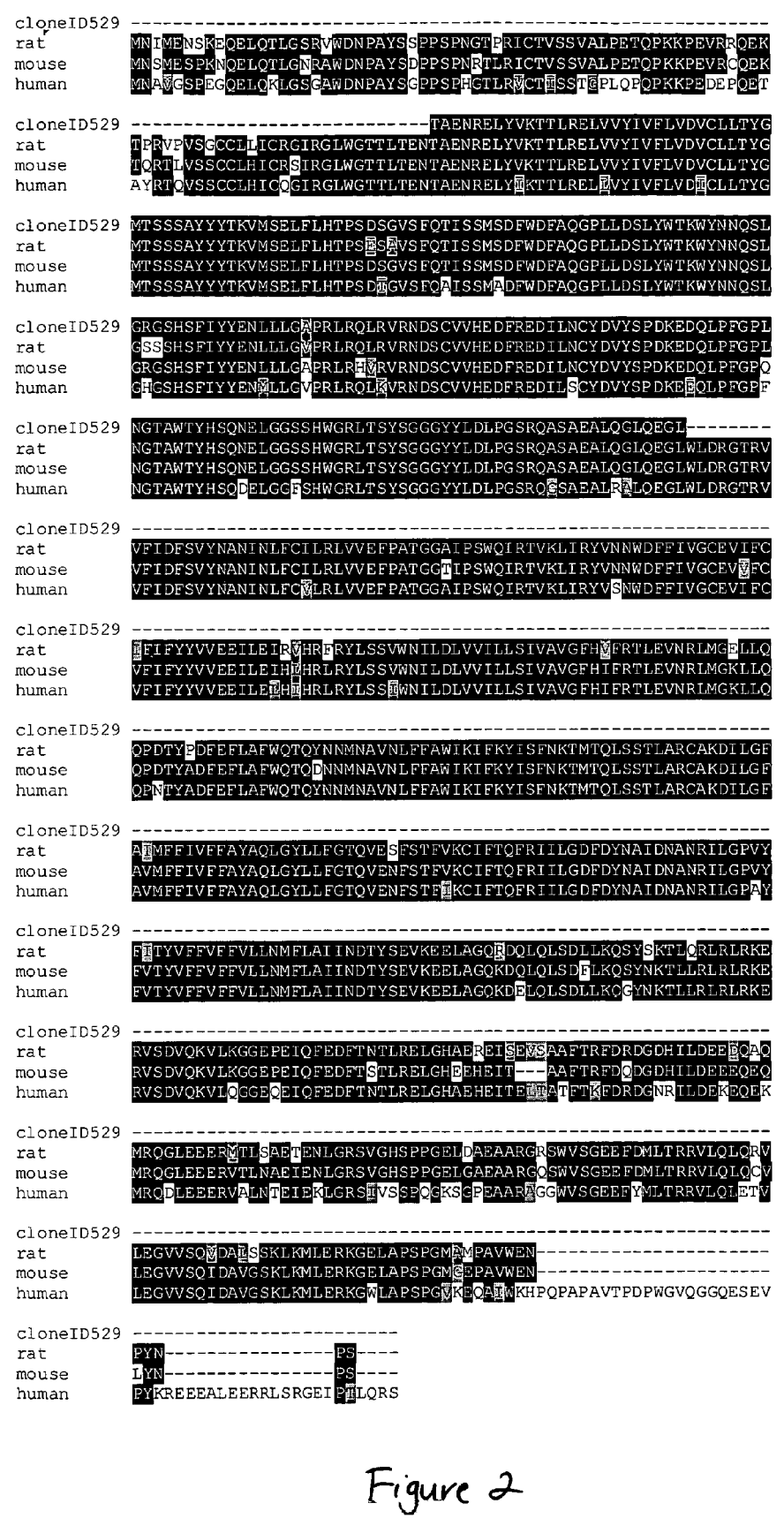

Analyses of mouse, rat, and human sequence databases showed that the clone defined by PCR primers "CloneID529-30/597-8" encodes PKD2L1, a distant member of the Polycystin Kidney Disease family of proteins (Nomura, et al. (1998) "Identification of PKDL, a novel polycystic kidney disease 2-like gene whose murine homologue is deleted in mice with kidney and retinal defects" *J. Biol. Chem.* 273: 25967-25973), referred to as the TRPP family (Lin and Corey (2005) "TRP channels in mechanosensation" *Curr Opin Neurobiol.* (Epub ahead of print). It is most similar to PKD2. The human gene was first identified by Wu et al. (Wu et al. (1998) "Identification of PKD2L, a Human PKD2-Related Gene: Tissue-specific Expression and Mapping to Chromosome 10q25" *Genomics* 54(3) 564-568), and the mouse ortholog was isolated in a search for new members of the PKD family (Basora et al. (2002) "Tissue and Cellular Localization of a Novel Polycystic Kidney Disease-Like Gene Product, Polycystin-L" *J. Am. Soc. Nephrol* 13:293-301). An alignment of sequences for human, rat, and mouse PKD2L1 is provided in FIG. 2. Included in the alignment is the match to a PCR fragment isolated from taste receptor cells (corresponding to exons 2-5), and used as the probe in the in situ studies shown in FIG. 1.

```
Mouse PKD2L1 fragment isolated from taste tissue
(exons 2-5) (SEQ ID NO:1):
DNA
ACAGCCGAGAACAGGGAGCTTTATGTCAAGACCACCCTGAGGGAGCTTGT

GGTATACATAGTGTTCCTCGTGGACGTCTGTCTGTTGACCTACGGAATGA

CAAGTTCTAGTGCCTATTACTACACCAAAGTGATGTCTGAGTTGTTCCTA

CACACCCCATCCGACTCTGGAGTCTCCTTCCAGACCATCAGCAGCATGTC

AGACTTCTGGGATTTTGCTCAGGGCCCACTCCTGGACAGTTTGTACTGGA

CAAAGTGGTACAACAACCAGAGCCTGGGGCGTGGCTCCCACTCCTTCATC

TACTATGAGAACCTGCTCCTGGGAGCCCCAAGGTTGCGGCAGCTGCGCGT

GCGCAATGACTCCTGTGTGGTTCATGAAGACTTCCGGGAGGACATTTTGA

ACTGTTATGATGTGTACTCGCCGGACAAAGAAGATCAGCTCCCCTTTGGA

CCTCTGAACGGCACAGCGTGGACATACCATTCCCAGAATGAGCTGGGTGG

CTCCTCCCACTGGGGCAGGCTCACAAGCTACAGCGGGGGTGGCTACTACT

TGGATCTTCCAGGATCCCGACAAGCCAGTGCAGAGGCCCTCCAAGGACTC
```

```
-continued

CAGGAGGGACTG
```

Taste tissue may also express PKD2L1 splice variants and may be present in PKD2L1 cDNA libraries.

```
Predicted Amino Acid sequence (SEQ ID NO:2)
TAENRELYVKTTLRELVVYIVFLVDVCLLTYGMTSSSAYYYTKVMSELFL

HTPSDSGVSFQTISSMSDFWDFAQGPLLDSLYWTKWYNNQSLGRGSHSFI

YYENLLLGAPRLRQLRVRNDSCVVHEDFREDILNCYDVYSPDKEDQLPFG

PLNGTAWTYHSQNELGGSSHWGRLTSYSGGGYYLDLPGSRQASAELQGLQ

EGL mouse PKD2L1 predicted mRNA (full-length, SEQ ID
NO:3)
ATGAAAGTATGGAAAGCCCCAAGAATCAGGAGCTACAAACCCTGGGGAAC

AGAGCCTGGGACAATCCTGCCTACAGCGACCCTCCTTCCCCGAACAGGAC

GCTGAGGATCTGCACTGTCTCCAGTGTGGCTCTCCCTGAGACTCAACCCA

AAAAGCCAGAAGTCAGATGCCAGGAGAAGACACAGAGAACCCTGGTGTCC

AGCTGCTGTCTCCATATCTGTCGGAGCATCAGAGGACTGTGGGGACAAC

GCTGACTGAGAACACAGCCGAGAACAGGGAGCTTTATGTCAAGACCACCC

TAAGGGAGCTTGTGGTATACATAGTGTTCCTCGTGGACGTCTGTCTGTTG

ACCTACGGAATGACAAGTTCTAGTGCCTATTACTACACCAAAGTGATGTC

TGAATTGTTTCTACACACCCCATCCGACTCTGGAGTCTCCTTCCAAACCA

TCAGCAGCATGTCAGACTTCTGGGATTTTGCTCAGGGCCCACTCCTGGAC

AGTTTGTACTGGACAAAGTGGTACAACAACCAGAGCCTGGGGCGTGGCTC

CCACTCCTTCATCTACTATGAGAACCTGCTCCTGGGAGCCCCAAGGTTGC

GGCACGTGCGCGTGCGCAATGACTCCTGTGTGGTTCATGAAGACTTCCGG

GAGGACATTTTGAACTGTTATGATGTGTACTCGCCGGACAAAGAAGATCA

GCTCCCCTTTGGACCTCAGAACGGCACAGCGTGGACATACCATTCCCAGA

ATGAGCTGGGTGGCTCCTCCCACTGGGGCAGGCTCACAAGCTACAGCGGG

GGTGGCTACTACTTGGATCTTCCAGGATCCCGACAAGCCAGTGCAGAGGC

CCTCCAAGGACTCCAGGAGGGACTGTGGCTGGACAGGGGCACTCGGGTGG

TCTTTATCGACTTCTCCGTCTACAATGCCAACATCAATCTTTTCTGTATT

CTGAGACTGGTGGTAGAGTTTCCAGCCACAGGAGGGACCATCCCATCCTG

GCAGATCCGCACAGTTAAGCTGATCCGCTATGTGAATAACTGGGACTTCT

TCATTGTGGGCTGTGAAGTTGTCTTCTGTGTCTTCATCTTCTATTATGTG

GTGGAGGAAATCCTGGAAATCCACCTGCATCGGCTTCGCTACCTCAGCAG

CGTCTGGAACATTCTGGACCTGGTGGTCATCTTGCTCTCCATCGTGGCTG

TGGGTTTCCACATATTCCGAACCCTGGAAGTGAACCGACTGATGGGAAAG

CTTCTGCAACAGCCAGACACGTATGCAGACTTTGAGTTCCTGGCCTTCTG

GCAGACTCAGGACAATAACATGAACGCGGTCAACCTTTTCTTTGCTTGGA

TCAAGATATTCAAGTATATCAGCTTCAACAAGACCATGACACAGCTCTCC

TCCACCCTGGCTCGATGTGCCAAGGACATCCTGGGCTTCGCAGTCATGTT

CTTCATTGTCTTCTTCGCTTACGCCCAGCTTGGTTACCTGCTTTTTGGGA
```

```
CCCAAGTGGAAAACTTTAGCACTTTCGTCAAGTGCATTTTCACTCAGTTC
CGGATAATCCTTGGGGATTTTGACTACAATGCCATCGACAATGCCAACAG
AATCCTGGGCCCTGTGTACTTTGTCACCTATGTCTTCTTCGTCTTCTTCG
TGCTCCTGAACATGTTCCTGGCCATCATCAACGACACATACTCCGAGGTC
AAGGAGGAGCTGGCTGGCCAGAAGGATCAGTTGCAGCTTTCTGACTTCCT
GAAACAGAGCTACAACAAGACCCTACTAAGGCTGCGCCTGAGGAAAGAGC
GGGTTTCTGATGTGCAGAAGGTCCTGAAGGGTGGGGAACCAGAGATCCAG
TTTGAAGATTTCACCAGCACCTTGAGGGAACTGGGGCACGAGGAGCACGA
GATCACCGCTGCCTTCACCAGGTTTGATCAGGATGGGGACCACATACTGG
ATGAGGAGGAGCAGGAACAGATGCGGCAGGGACTGGAAGAGGAGAGGGTG
ACCCTCAATGCTGAGATTGAGAACCTAGGCCGGTCTGTTGGACACAGCCC
CCCAGGCGAATTGGGCGCGGAGGCTGCCAGAGGACAAAGCTGGGTTTCTG
GAGAAGAATTCGACATGCTCACAAGGAGAGTTCTGCAGCTGCAGTGTGTT
CTGGAAGGAGTTGTGTCCCAGATTGATGCTGTAGGCTCAAAGCTGAAGAT
GCTGGAGAGGAAAGGGGAGCTGGCTCCCTCCCCAGGAATGGGGGAACCAG
CTGTTTGGGAGAACCTGTATAATCCGTCCTAGT
human PKD2L1 taste predicted mRNA sequence (full-
length, SEQ ID NO:4):
ATGAATGCTGTGGGAAGTCCTGAGGGGCAGGAGCTGCAAAAGCTGGGGAG
TGGAGCCTGGGACAACCCCGCCTACAGTGGTCCCCCTTCCCCACACGGGA
CGCTGAGAGTCTGCACCATCTCCAGCACGGGGCCTCTCCAGCCCCAACCC
AAGAAGCCTGAAGATGAACCCCAGGAGACGGCATACAGGACCCAGGTGTC
CAGCTGCTGCCTCCATATCTGTCAAGGCATCAGAGGACTTTGGGGAACAA
CCCTGACTGAGAACACAGCTGAGAACCGGGAACTTTATATCAAGACCACC
CTGAGGGAGCTGTTGGTATATATTGTGTTCCTGGTGGACATCTGTCTACT
GACCTATGGAATGACAAGCTCCAGTGCTTATTACTACACCAAAGTGATGT
CTGAGCTCTTCTTACATACTCCATCAGACACTGGAGTCTCCTTTCAGGCC
ATCAGCAGCATGGCGGACTTCTGGGATTTTGCCCAGGGCCCACTACTGGA
CAGTTTGTATTGGACCAAATGGTACAACAACCAGAGCCTGGGCCATGGCT
CCCACTCCTTCATCTACTATGAGAACATGCTGCTGGGGGTTCCGAGGCTG
CGGCAGCTAAAGGTCCGCAATGACTCCTGTGTGGTGCATGAAGACTTCCG
GGAGGACATTCTGAGCTGCTATGATGTCTACTCTCCAGACAAAGAAGAAC
AACTCCCCTTTGGGCCCTTCAATGGCACAGCGTGGACATACCACTCGCAG
GATGAGTTGGGGGGCTTCTCCCACTGGGGCAGGCTCACAAGCTACAGCGG
AGGTGGCTACTACCTGGACCTTCCAGGATCCCGACAGGGTAGTGCAGAGG
CTCTCCGGGCCCTTCAGGAGGGGCTGTGGCTGGACAGGGGCACTCGAGTG
GTGTTCATCGACTTCTCAGTCTACAATGCCAATATCAATCTTTTCTGTGT
CCTGAGGCTGGTGGTGGAGTTTCCAGCTACAGGAGGTGCCATCCCATCCT
GGCAAATCCGCACAGTCAAGCTGATCCGCTATGTCAGCAACTGGGACTTC
TTTATCGTTGGCTGTGAGGTCATCTTCTGCGTCTTCATCTTCTACTATGT
GGTGGAAGAGATCCTGGAGCTCCACATTCACCGGCTTCGCTACCTCAGCA GCATCTGGAACATACTGGACCTGGTGGTCATCTTGCTCTCCATTGTGGCT
GTGGGCTTCCACATATTCCGAACCCTCGAGGTGAATCGGCTCATGGGGAA
GCTCCTGCAGCAGCCAAACACGTATGCAGACTTTGAGTTCCTCGCCTTCT
GGCAGACACAGTACAACAACATGAATGCTGTCAACCTCTTCTTCGCCTGG
ATCAAGATATTCAAGTACATCAGCTTCAACAAAACCATGACCCAGCTCTC
CTCCACGCTGGCCCGCTGTGCCAAGGACATCCTGGGCTTCGCCGTCATGT
TCTTCATTGTTTTCTTCGCCTATGCCCAACTCGGCTACCTGCTTTTCGGG
ACCCAAGTGGAAAACTTTAGCACTTTCATCAAGTGCATTTTCACTCAGTT
CCGGATAATCCTCGGGGACTTTGACTACAATGCTATCGACAATGCCAACC
GCATCCTGGGCCCTGCCTACTTTGTCACCTATGTCTTCTTCGTCTTCTTC
GTGCTCCTGAACATGTTCCTGGCCATCATCAATGACACATATTCAGAGGT
CAAGGAGGAGCTGGCTGGACAGAAGGATGAGCTGCAACTTTCTGACCTCC
TGAAACAGGGCTACAACAAGACCCTACTAAGGACTGCGTCTGAGGAAGGAG
AGGGTTTCGGATGTGCAGAAGGTCCTGCAGGGTGGGGAGCAGGAGATCCA
GTTTGAGGATTTCACCAACACCTTAAGGGAACTGGGACACGCAGAGCATG
AAATACTGAGCTCACGGCCACCTTCACCAAGTTTGACAGAGATGGGAAT
CGTATTCTGGATGAGAAGGAACAGGAAAAAATGCGACAGGACCTGGAGGA
AGAGAGGGTGGCCCTCAACACTGAGATTGAGAAACTAGGCCGATCTATTG
TGAGCAGCCCACAAGGCAAATCGGGTCCAGAGGCTGCCAGAGCAGGAGGC
TGGGTTTCAGGAGAAGAATTCTACATGCTCACAAGGAGAGTTCTGCAGCT
GGAGACTGTCCTGGAAGGAGTAGTGTCCCAGATTGATGCTGTAGGCTCAA
AGCTGAAAATGCTGGAGAGGAAGGGGTGGCTGGCTCCCTCCCCAGGCGTG
AAGGAACAAGCTATTTGGAAGCACCCGCAGCCAGCCCCAGCTGTGACCCC
AGACCCCTGGGGAGTCCAGGGTGGGCAGGAGAGTGAGGTTCCCTATAAAA
GAGAAGAGGAAGCCTTAGAGGAGAGGAGACTCTCCCGTGGTGAGATTCCA
ACGTTGCAGAGGAGTTAA
```

Ensembl predicts an ortholog in the Dog genome:
geneID < ENSCAFG00000009644 > (SEQ ID NO:5)
MNAVESPEGQELQKMGSGAWDNPAYSGPPSPRGTLKICTISSAMPPQPQI
QKPEDGPQEKAYRTLVSSCCFQICRGIRGLWGTTLTENTAENRELYVKTT
LRELLVYIVFLVDICLLTYGMTSSSAYYYTKVMSELFLHTPSDTGVSFQA
ISSMADFWDFAQGPLLDSLYWTKWYNNQSLGHGSHSFIYYENLLLGVPRL
RQLRVRNDSCVVHEDFREDILSCYDVYSPDKEEQLPFGPLNGTAWTYHSQ
DELGGSSHWGRLTSYSGGGYYLDLPGSRQASAEALQDLQEGLWLDRGTRV
VFIDFSVYNANINLFCVLRLVVEFPATGGAIPSWQIRTVKLIRYVSNWDF
FIIGCEIIFCIFIVYYMVEEILELHIHRLHYLSSIWNILDLVVIMLSIVA
VGFHIFRTLEVNRLMGKLLQQPNMYADFEFLAFWQTQYNNMNAVNLFFAW
IKIFKYISFNKTMTQLSSTLARCAKDILGFAVMFFIVFFAYAQLGYLLFG
TQVENFSTFIKCIFTQFRIILGDFDYNAIDNANRILGPAYFVTYVFFVFF
VLLNMFLAIINDTYSEVKEELAGQKDELQLSDLLKQGYNKTLLRLRLRKE
RVSDVQKVLQGGEQEIQFEDFTNTLRELGHAEHEITELTAAFTRFDQDGN -continued

HILDKKEQEQMQQDLEEKRVVLNAEIENLGQSIVSSSPGESGPEATRADG

WVSGEEFYTLTRRVLQLETVLEGVMSQVDAVGSKLEMLERKEQLASSPGM

GDQGIWEHLQPTSPVTPDPWGVQGGQESEFPGGREGEALEEMRLS

ADDITIONAL REFERENCES

Liu et al. (2002) "Modulation of the human polycystin-L channel by voltage and divalent cations" *FEBS Letters* 525 (1-3) 71-76; Keller et al. (1994) "Kidney and Retinal Defects (Krd), a Transgene-Induced Mutation with a Deletion of Mouse Chromosome 19 That Includes the Pax2 Locus" *Genomics* 23: 309-320; Gilbertson, T. (1993) The physiology of vertebrate taste reception 3, 532-539; Kinnamon and Margolskee (1996), *Curr. Opin. Neurobiol.* 4:506-513; Adler et al. (2000) "A novel family of mammalian taste receptors" *Cell* 100:693-702; Chandrashekar et al. (2000) "T2Rs function as bitter taste receptors" *Cell* 100:703-711.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method of identifying a compound that binds to or modulates an activity of a polycystin-2L1 taste receptor polypeptide, the method comprising:
   (a.) contacting a biological or biochemical sample comprising the polycystin-2L1 taste receptor polypeptide with a test compound; and,
   (b.) detecting binding of the test compound to the polycystin-2L1 taste receptor polypeptide, or modulation of the activity of the polypeptide by the test compound, thereby identifying the compound which binds to or modulates the activity of the polycystin-2L1 taste receptor polypeptide.

2. The method of claim 1, wherein (a.) comprises contacting one or more biological sample comprising one or more polycystin-2L1 taste receptor polypeptides with a plurality of test compounds and wherein (b.) comprises detecting binding of the test compounds to the polycystin-2L1 taste receptor polypeptides, or modulation of the activity of the polypeptides by the test compounds, thereby identifying one or more compounds that binds to or modulates the activity of the polycystin-2L1 taste receptor polypeptides.

3. The method of claim 2, wherein the plurality of test compounds comprises a plurality of pre-screened compounds.

4. The method of claim 1, wherein the test compound is selected from the group consisting of: naturally occurring compounds, ions, sour tastants, small organic molecules, peptides, peptide mimetics, a weak acid, $CO_2$, acetic acid, a specific blocker of carbonic anhydrase, and MK-417.

5. The method of claim 1, wherein the test compound enhances an activity of the polycystin-2L1 taste receptor polypeptide.

6. The method of claim 1, wherein the test compound potentiates an activity of the polycystin-2L1 taste receptor polypeptide.

7. The method of claim 1, wherein the test compound inhibits or blocks an activity of the polycystin-2L1 taste receptor polypeptide.

8. The method of claim 1, wherein the polycystin-2L1 taste receptor polypeptide is a human polycystin-2L1 taste receptor polypeptide.

9. The method of claim 1, wherein the polycystin-2L1 taste receptor polypeptide is a murine polycystin-2L1 taste receptor polypeptide.

10. The method of claim 1, wherein the polycystin-2L1 taste receptor polypeptide is a polycystin-2L1 taste receptor polypeptide from a domesticated or livestock animal.

11. The method of claim 1, wherein step (b.) includes detecting binding between the polycystin-2L1 taste receptor polypeptide and a moiety selected from the group consisting of: a potentiator of the polycystin-2L1 taste receptor polypeptide, an antagonist of the polycystin-2L1 taste receptor polypeptide, an agonist of the polycystin-2L1 taste receptor polypeptide, an inverse agonist of the polycystin-2L1 taste receptor polypeptide, a ligand that specifically binds to the polycystin-2L1 taste receptor polypeptide, and an antibody that specifically binds to the polycystin-2L1 taste receptor polypeptide.

12. The method of claim 1, wherein step (b.) includes in situ or in vivo detection of the polycystin-2L1 taste receptor polypeptide.

13. The method of claim 1, wherein step (b.) includes detecting a signal resulting from the activity of the polycystin-2L1 taste receptor polypeptide.

14. The method of claim 13, wherein the signal is a conformation-dependent signal, wherein a conformation of the polycystin-2L1 taste receptor polypeptide is modified by binding of the test compound to the polycystin-2L1 taste receptor polypeptide.

15. The method of claim 1, wherein the biological sample comprises or is derived from a cell that expresses the polycystin-2L1 taste receptor polypeptide.

16. The method of claim 15, wherein detecting binding of the test compound to the polycystin-2L1 taste receptor polypeptide, or activity of the test compound on the polycystin-2L1 taste receptor polypeptide comprises detecting one or more of: $H^+$ flux, $Na^+$ flux, $Ca^{2+}$ flux, ion flux, depolarization of the cell, cell membrane voltage changes, cell membrane conductivity changes, a kinase activity triggered upon binding of a compound to the polycystin-2L1 taste receptor polypeptide, generation, breakdown or binding of a phorbol ester by the polycystin-2L1 taste receptor polypeptide, binding of diacylglycerol or other lipids by the polycystin-2L1 taste receptor polypeptide, cAMP activity, cGMP activity, GTPgammaS binding, phospholipase C activity, activity of an enzyme involved in cellular ionic balance, binding of polycystin-2L1 to another PKD protein, or a transcriptional reporter activity.

17. The method of claim 1, further comprising recombinantly expressing a PKD2L1 gene in a recombinant cell, wherein the biological sample is derived from the recombinant cell.

18. The method of claim 17, wherein the PKD2L1 gene is heterologous to the recombinant cell.

19. The method of claim 18, wherein the cell is a human, rodent or insect cell, and wherein the cell is a cell in culture or a primary cell.

20. The method of claim 17, wherein the cell is a taste bud or kidney cell, or wherein the cell is a cell derived from a taste bud or kidney cell.

21. The method of claim 1, wherein the polycystin-2L1 taste receptor polypeptide is incorporated into a biosensor.

22. The method of claim 21, wherein the biosensor comprises a Chem-FET.

23. A system for detecting compounds that bind to or modulate an activity of a polycystin-2L1 taste receptor polypeptide, the system comprising:
 (a.) a biological sample comprising the polycystin-2L1 taste receptor polypeptide;
 (b.) a source of a plurality of test compounds; and,
 (c.) a detector that detects binding of one or more of the test compounds to the polycystin-2L1 taste receptor polypeptide, or modulation of the activity of the polypeptide by one or more of the test compounds, thereby identifying a putative tastant compound that binds to or modulates the activity of the polycystin-2L1 taste receptor polypeptide.

24. The system of claim 23, wherein the biological sample comprises a cell comprising a heterologous gene encoding the polycystin-2L1 taste receptor polypeptide.

25. The system of claim 24, wherein the cell is selected from the group consisting of: a mammalian cell, an insect cell, a *Xenopus* cell, and a taste receptor cell.

26. The system of claim 23, wherein the source of test compounds comprises a library of tastant compounds.

27. The system of claim 23, wherein the source of test compounds comprises a pre-screened library of compounds.

28. The system of claim 23, wherein the detector comprises a patch clamp device or an optical detection device.

29. The system of claim 23, wherein the detector comprises a flourescence detector that detects FRET, changes in membrane potential or flow of a dye into or out of the cell.

* * * * *

SEQUENCE LISTING

```
<160> NUMBER OF SEQ ID NOS: 8

<210> SEQ ID NO 1
<211> LENGTH: 612
<212> TYPE: DNA
<213> ORGANISM: Mus musculus

<400> SEQUENCE: 1
acagccgaga acagggagct ttatgtcaag accaccctga gggagcttgt ggtatacata    60
gtgttcctcg tggacgtctg tctgttgacc tacggaatga caagttctag tgcctattac   120
tacaccaaag tgatgtctga gttgttccta cacaccccat ccgactctgg agtctccttc   180
cagaccatca gcagcatgtc agacttctgg gattttgctc agggcccact cctggacagt   240
ttgtactgga caaagtggta caacaaccag agcctggggc gtggctccca ctccttcatc   300
tactatgaga acctgctcct gggagcccca aggttgcggc agctgcgcgt gcgcaatgac   360
tcctgtgtgg ttcatgaaga cttccgggag gacattttga actgttatga tgtgtactcg   420
ccggacaaag aagatcagct cccctttgga cctctgaacg gcacagcgtg gacataccat   480
tcccagaatg agctgggtgg ctcctcccac tggggcaggc tcacaagcta cagcgggggt   540
ggctactact tggatcttcc aggatcccga caagccagtg cagaggccct ccaaggactc   600
caggagggac tg                                                        612

<210> SEQ ID NO 2
<211> LENGTH: 204
<212> TYPE: PRT
<213> ORGANISM: Mus musculus

<400> SEQUENCE: 2

Thr Ala Glu Asn Arg Glu Leu Tyr Val Lys Thr Thr Leu Arg Glu Leu
1               5                   10                  15

Val Val Tyr Ile Val Phe Leu Val Asp Val Cys Leu Leu Thr Tyr Gly
            20                  25                  30

Met Thr Ser Ser Ala Tyr Tyr Tyr Thr Lys Val Met Ser Glu Leu
        35                  40                  45

Phe Leu His Thr Pro Ser Asp Ser Gly Val Ser Phe Gln Thr Ile Ser
    50                  55                  60

Ser Met Ser Asp Phe Trp Asp Phe Ala Gln Gly Pro Leu Leu Asp Ser
65                  70                  75                  80
```

```
Leu Tyr Trp Thr Lys Trp Tyr Asn Asn Gln Ser Leu Gly Arg Gly Ser
                 85                  90                  95
His Ser Phe Ile Tyr Tyr Glu Asn Leu Leu Leu Gly Ala Pro Arg Leu
            100                 105                 110
Arg Gln Leu Arg Val Arg Asn Asp Ser Cys Val Val His Glu Asp Phe
        115                 120                 125
Arg Glu Asp Ile Leu Asn Cys Tyr Asp Val Tyr Ser Pro Asp Lys Glu
    130                 135                 140
Asp Gln Leu Pro Phe Gly Pro Leu Asn Gly Thr Ala Trp Thr Tyr His
145                 150                 155                 160
Ser Gln Asn Glu Leu Gly Gly Ser Ser His Trp Gly Arg Leu Thr Ser
                165                 170                 175
Tyr Ser Gly Gly Gly Tyr Tyr Leu Asp Leu Pro Gly Ser Arg Gln Ala
            180                 185                 190
Ser Ala Glu Ala Leu Gln Gly Leu Gln Glu Gly Leu
        195                 200
```

<210> SEQ ID NO 3
<211> LENGTH: 2283
<212> TYPE: DNA
<213> ORGANISM: Mus musculus

<400> SEQUENCE: 3

```
atgaaagtat ggaaagcccc aagaatcagg agctacaaac cctggggaac agagcctggg      60
acaatcctgc ctacagcgac cctccttccc gaacaggac gctgaggatc tgcactgtct      120
ccagtgtggc tctccctgag actcaaccca aaaagccaga agtcagatgc aggagaaga      180
cacagagaac cctggtgtcc agctgctgtc tccatatctg tcggagcatc agaggactgt      240
gggggacaac gctgactgag aacacagccg agaacaggga gctttatgtc aagaccaccc      300
taagggagct tgtggtatac atagtgttcc tcgtggacgt ctgtctgttg acctacggaa      360
tgacaagttc tagtgcctat tactacacca agtgatgtc tgaattgttt ctacacaccc      420
catccgactc tggagtctcc ttccaaacca tcagcagcat gtcagacttc tgggattttg      480
ctcagggccc actcctggac agtttgtact ggacaaagtg gtacaacaac agagcctgg      540
ggcgtggctc ccactccttc atctactatg agaacctgct cctgggagcc ccaaggttgc      600
ggcacgtgcg cgtgcgcaat gactcctgtg tggttcatga agacttccgg gaggacattt      660
tgaactgtta tgatgtgtac tcgccggaca agaagatca gctccccttt ggacctcaga      720
acggcacagc gtggacatac cattcccaga tgagctgg tggctcctcc cactggggca      780
ggctcacaag ctacagcggg ggtggctact acttggatct tccaggatcc gacaagcca      840
gtgcagaggc cctccaagga ctccaggagg gactgtggct ggacaggggc actcgggtgg      900
tctttatcga cttctccgtc tacaatgcca acatcaatct tttctgtatt ctgagactgg      960
tggtagagtt ccagccaca ggagggacca tcccatcctg gcagatccgc acagttaagc      1020
tgatccgcta tgtgaataac tgggacttct tcattgtggg ctgtgaagtt gtcttctgtg      1080
tcttcatctt ctattatgtg gtggaggaaa tcctggaaat ccacctgcat cggcttcgct      1140
acctcagcag cgtctggaac attctggacc tggtggtcat cttgctctcc atcgtggctg      1200
tgggtttcca catattccga accctggaag tgaaccgact gatgggaaag cttctgcaac      1260
agccagacac gtatgcagac tttgagttcc tggccttctg gcagactcag gacaataaca      1320
tgaacgcggt caacctttc tttgcttgga tcaagatatt caagtatatc agcttcaaca      1380
agaccatgac acagctctcc tccacccctg gctcgatgtg caaggacatc ctgggcttcg      1440
```

```
cagtcatgtt cttcattgtc ttcttcgctt acgcccagct tggttacctg cttttggga    1500 cccaagtgga aaactttagc actttcgtca agtgcatttt cactcagttc cggataatcc    1560
ttggggattt tgactacaat gccatcgaca atgccaacag aatcctgggc cctgtgtact    1620
ttgtcaccta tgtcttcttc gtcttcttcg tgctcctgaa catgttcctg ccatcatca    1680 acgacacata ctccgaggtc aaggaggagc tggctggcca aaggatcag ttgcagcttt    1740 ctgacttcct gaaacagagc tacaacaaga ccctactaag gctgcgcctg aggaaagagc    1800
gggtttctga tgtgcagaag gtcctgaagg gtggggaacc agagatccag tttgaagatt    1860
tcaccagcac cttgagggaa ctggggcacg aggagcacga gatcaccgct gccttcacca    1920
ggtttgatca ggatgggac cacatactgg atgaggagga gcaggaacag atgcggcagg    1980
gactggaaga ggagagggtg accctcaatg ctgagattga aacctaggc cggtctgttg    2040 gacacagccc cccaggcgaa ttgggcgcgg aggctgccag aggacaaagc tgggtttctg    2100
gagaagaatt cgacatgctc acaaggagag ttctgcagct gcagtgtgtt ctggaaggag    2160
ttgtgtccca gattgatgct gtaggctcaa agctgaagat gctggagagg aaagggagc    2220 tggctccctc cccaggaatg ggggaaccag ctgtttggga gaacctgtat aatccgtcct    2280
agt                                                                  2283

<210> SEQ ID NO 4
<211> LENGTH: 2418
<212> TYPE: DNA
<213> ORGANISM: Homo sapiens

<400> SEQUENCE: 4
atgaatgctg tgggaagtcc tgaggggcag gagctgcaaa agctggggag tggagcctgg    60
gacaaccccg cctacagtgg tccccttcc ccacacggga cgctgagagt ctgcaccatc    120
tccagcacgg ggcctctcca gccccaaccc aagaagcctg aagatgaacc ccaggagacg    180
gcatacagga cccaggtgtc cagctgctgc ctccatatct gtcaaggcat cagaggactt    240
tggggaacaa ccctgactga aacacagct gagaaccggg aactttatat caagaccacc    300
ctgagggagc tgttggtata tattgtgttc ctggtggaca tctgtctact gacctatgga    360
atgcaaagct ccagtgctta ttactacacc aaagtgatgt ctgagctctt cttacatact    420
ccatcagaca ctggagtctc ctttcaggcc atcagcagca tggcggactt ctgggatttt    480
gcccagggcc cactactgga cagtttgtat tggaccaaat ggtacaacaa ccagagcctg    540
ggccatggct cccactcctt catctactat gagaacatgc tgctgggggt tccgaggctg    600
cggcagctaa aggtccgcaa tgactcctgt gtggtgcatg aagacttccg ggaggacatt    660
ctgagctgct atgatgtcta ctctccagac aaagaagaac aactccccct tgggcccttc    720
aatggcacag cgtggacata ccactcgcag gatgagttgg ggggcttctc ccactggggc    780
aggctcacaa gctacagcgg aggtggctac tacctggacc ttccaggatc ccgacagggt    840
agtgcagagg ctctccgggc ccttcaggag gggctgtggc tggacagggg cactcgagtg    900
gtgttcatcg acttctcagt ctacaatgcc aatatcaatc ttttctgtgt cctgaggctg    960
gtggtggagt ttccagctac aggaggtgcc atcccatcct ggcaaatccg cacagtcaag   1020
ctgatccgct atgtcagcaa ctgggactc tttatcgttg ctgtgaggt catcttctgc   1080 gtcttcatct tctactatgt ggtggaagag atcctggagc tccacattca ccggcttcgc   1140
tacctcagca gcatctggaa catactggac ctggtggtca tcttgctctc cattgtggct   1200
```

-continued

| | |
|---|---|
| gtgggcttcc acatattccg aaccctcgag gtgaatcggc tcatggggaa gctcctgcag | 1260 |
| cagccaaaca cgtatgcaga ctttgagttc ctcgccttct ggcagacaca gtacaacaac | 1320 |
| atgaatgctg tcaacctctt cttcgcctgg atcaagatat tcaagtacat cagcttcaac | 1380 |
| aaaaccatga cccagctctc ctccacgctg gcccgctgtg ccaaggacat cctgggcttc | 1440 |
| gccgtcatgt tcttcattgt tttcttcgcc tatgcccaac tcggctacct gcttttcggg | 1500 |
| acccaagtgg aaaactttag cactttcatc aagtgcattt tcactcagtt ccggataatc | 1560 |
| ctcggggact tgactacaa tgctatcgac aatgccaacc gcatcctggg ccctgcctac | 1620 |
| tttgtcacct atgtcttctt cgtcttcttc gtgctcctga acatgttcct ggccatcatc | 1680 |
| aatgacacat attcagaggt caaggaggag ctggctggac agaaggatga gctgcaactt | 1740 |
| tctgacctcc tgaaacaggg ctacaacaag accctactaa gactgcgtct gaggaaggag | 1800 |
| agggtttcgg atgtgcagaa ggtcctgcag ggtggggagc aggagatcca gtttgaggat | 1860 |
| ttcaccaaca ccttaaggga actgggacac gcagagcatg aaatcactga gctcacggcc | 1920 |
| accttcacca gtttgacag agatgggaat cgtattctgg atgagaagga acaggaaaaa | 1980 |
| atgcgacagg acctggagga agagagggtg ccctcaaca ctgagattga aaactaggc | 2040 |
| cgatctattg tgagcagccc acaaggcaaa tcgggtccag aggctgccag agcaggaggc | 2100 |
| tgggtttcag agaagaatt ctacatgctc acaaggagag ttctgcagct ggagactgtc | 2160 |
| ctggaaggag tagtgtccca gattgatgct gtaggctcaa agctgaaaat gctggagagg | 2220 |
| aaggggtggc tggctccctc cccaggcgtg aaggaacaag ctatttggaa gcacccgcag | 2280 |
| ccagccccag ctgtgacccc agacccctgg ggagtccagg gtgggcagga gagtgaggtt | 2340 |
| ccctataaaa gagaagagga agccttagag gagaggagac tctcccgtgg tgagattcca | 2400 |
| acgttgcaga ggagttaa | 2418 |

<210> SEQ ID NO 5
<211> LENGTH: 795
<212> TYPE: PRT
<213> ORGANISM: Canis familiaris

<400> SEQUENCE: 5

```
Met Asn Ala Val Glu Ser Pro Glu Gly Gln Glu Leu Gln Lys Met Gly
1               5                  10                  15

Ser Gly Ala Trp Asp Asn Pro Ala Tyr Ser Gly Pro Ser Pro Arg
            20                  25                  30

Gly Thr Leu Lys Ile Cys Thr Ile Ser Ser Ala Met Pro Pro Gln Pro
        35                  40                  45

Gln Ile Gln Lys Pro Glu Asp Gly Pro Gln Glu Lys Ala Tyr Arg Thr
    50                  55                  60

Leu Val Ser Ser Cys Cys Phe Gln Ile Cys Arg Gly Ile Arg Gly Leu
65                  70                  75                  80

Trp Gly Thr Thr Leu Thr Glu Asn Thr Ala Glu Asn Arg Glu Leu Tyr
                85                  90                  95

Val Lys Thr Thr Leu Arg Glu Leu Leu Val Tyr Ile Val Phe Leu Val
            100                 105                 110

Asp Ile Cys Leu Leu Thr Tyr Gly Met Thr Ser Ser Ala Tyr Tyr
        115                 120                 125

Tyr Thr Lys Val Met Ser Glu Leu Phe Leu His Thr Pro Ser Asp Thr
    130                 135                 140

Gly Val Ser Phe Gln Ala Ile Ser Ser Met Ala Asp Phe Trp Asp Phe
145                 150                 155                 160
```

```
Ala Gln Gly Pro Leu Leu Asp Ser Leu Tyr Trp Thr Lys Trp Tyr Asn
                165                 170                 175

Asn Gln Ser Leu Gly His Gly Ser His Ser Phe Ile Tyr Tyr Glu Asn
            180                 185                 190

Leu Leu Leu Gly Val Pro Arg Leu Arg Gln Leu Arg Val Arg Asn Asp
        195                 200                 205

Ser Cys Val Val His Glu Asp Phe Arg Glu Asp Ile Leu Ser Cys Tyr
    210                 215                 220

Asp Val Tyr Ser Pro Asp Lys Glu Glu Gln Leu Pro Phe Gly Pro Leu
225                 230                 235                 240

Asn Gly Thr Ala Trp Thr Tyr His Ser Gln Asp Glu Leu Gly Gly Ser
                245                 250                 255

Ser His Trp Gly Arg Leu Thr Ser Tyr Ser Gly Gly Tyr Tyr Leu
                260                 265                 270

Asp Leu Pro Gly Ser Arg Gln Ala Ser Glu Ala Leu Gln Asp Leu
            275                 280                 285

Gln Glu Gly Leu Trp Leu Asp Arg Gly Thr Arg Val Val Phe Ile Asp
    290                 295                 300

Phe Ser Val Tyr Asn Ala Asn Ile Asn Leu Phe Cys Val Leu Arg Leu
305                 310                 315                 320

Val Val Glu Phe Pro Ala Thr Gly Gly Ala Ile Pro Ser Trp Gln Ile
                325                 330                 335

Arg Thr Val Lys Leu Ile Arg Tyr Val Ser Asn Trp Asp Phe Phe Ile
            340                 345                 350

Ile Gly Cys Glu Ile Ile Phe Cys Ile Phe Ile Val Tyr Tyr Met Val
        355                 360                 365

Glu Glu Ile Leu Glu Leu His Ile His Arg Leu His Tyr Leu Ser Ser
    370                 375                 380

Ile Trp Asn Ile Leu Asp Leu Val Val Ile Met Leu Ser Ile Val Ala
385                 390                 395                 400

Val Gly Phe His Ile Phe Arg Thr Leu Glu Val Asn Arg Leu Met Gly
                405                 410                 415

Lys Leu Leu Gln Gln Pro Asn Met Tyr Ala Asp Phe Glu Phe Leu Ala
            420                 425                 430

Phe Trp Gln Thr Gln Tyr Asn Asn Met Asn Ala Val Asn Leu Phe Phe
        435                 440                 445

Ala Trp Ile Lys Ile Phe Lys Tyr Ile Ser Phe Asn Lys Thr Met Thr
    450                 455                 460

Gln Leu Ser Ser Thr Leu Ala Arg Cys Ala Lys Asp Ile Leu Gly Phe
465                 470                 475                 480

Ala Val Met Phe Phe Ile Val Phe Phe Ala Tyr Ala Gln Leu Gly Tyr
                485                 490                 495

Leu Leu Phe Gly Thr Gln Val Glu Asn Phe Ser Thr Phe Ile Lys Cys
            500                 505                 510

Ile Phe Thr Gln Phe Arg Ile Ile Leu Gly Asp Phe Asp Tyr Asn Ala
        515                 520                 525

Ile Asp Asn Ala Asn Arg Ile Leu Gly Pro Ala Tyr Phe Val Thr Tyr
    530                 535                 540

Val Phe Phe Val Phe Phe Val Leu Leu Asn Met Phe Leu Ala Ile Ile
545                 550                 555                 560

Asn Asp Thr Tyr Ser Glu Val Lys Glu Glu Leu Ala Gly Gln Lys Asp
                565                 570                 575
```

-continued

```
Glu Leu Gln Leu Ser Asp Leu Leu Lys Gln Gly Tyr Asn Lys Thr Leu
                580                 585                 590

Leu Arg Leu Arg Leu Arg Lys Glu Arg Val Ser Asp Val Gln Lys Val
            595                 600                 605

Leu Gln Gly Gly Glu Gln Glu Ile Gln Phe Glu Asp Phe Thr Asn Thr
        610                 615                 620

Leu Arg Glu Leu Gly His Ala Glu His Glu Ile Thr Glu Leu Thr Ala
625                 630                 635                 640

Ala Phe Thr Arg Phe Asp Gln Asp Gly Asn His Ile Leu Asp Lys Lys
                645                 650                 655

Glu Gln Glu Gln Met Gln Asp Leu Glu Lys Arg Val Val Leu
            660                 665                 670

Asn Ala Glu Ile Glu Asn Leu Gly Gln Ser Ile Val Ser Ser Pro
        675                 680                 685

Gly Glu Ser Gly Pro Glu Ala Thr Arg Ala Asp Gly Trp Val Ser Gly
    690                 695                 700

Glu Glu Phe Tyr Thr Leu Thr Arg Arg Val Leu Gln Leu Glu Thr Val
705                 710                 715                 720

Leu Glu Gly Val Met Ser Gln Val Asp Ala Val Gly Ser Lys Leu Glu
                725                 730                 735

Met Leu Glu Arg Lys Glu Gln Leu Ala Ser Ser Pro Gly Met Gly Asp
            740                 745                 750

Gln Gly Ile Trp Glu His Leu Gln Pro Thr Ser Pro Val Thr Pro Asp
        755                 760                 765

Pro Trp Gly Val Gln Gly Gln Glu Ser Glu Phe Pro Gly Gly Arg
    770                 775                 780

Glu Gly Glu Ala Leu Glu Glu Met Arg Leu Ser
785                 790                 795

<210> SEQ ID NO 6
<211> LENGTH: 763
<212> TYPE: PRT
<213> ORGANISM: Rattus norvegicus

<400> SEQUENCE: 6

Met Asn Ile Met Glu Asn Ser Lys Glu Gln Glu Leu Gln Thr Leu Gly
1               5                   10                  15

Ser Arg Val Trp Asp Asn Pro Ala Tyr Ser Pro Ser Pro Ser Pro Asn
                20                  25                  30

Gly Thr Pro Arg Ile Cys Thr Val Ser Ser Val Ala Leu Pro Glu Thr
            35                  40                  45

Gln Pro Lys Lys Pro Glu Val Arg Arg Gln Glu Lys Thr Pro Arg Val
        50                  55                  60

Pro Val Ser Gly Cys Cys Leu Leu Ile Cys Arg Ser Ile Arg Gly Leu
65                  70                  75                  80

Trp Gly Thr Thr Leu Thr Glu Asn Thr Ala Glu Asn Arg Glu Leu Tyr
                85                  90                  95

Val Lys Thr Thr Leu Arg Glu Leu Val Val Tyr Ile Val Phe Leu Val
            100                 105                 110

Asp Val Cys Leu Leu Thr Tyr Gly Met Thr Ser Ser Ser Ala Tyr Tyr
        115                 120                 125

Tyr Thr Lys Val Met Ser Glu Leu Phe Leu His Thr Pro Ser Glu Ser
    130                 135                 140

Ala Val Ser Phe Gln Thr Ile Ser Ser Met Ser Asp Phe Trp Asp Phe
145                 150                 155                 160
```

```
Ala Gln Gly Pro Leu Leu Asp Ser Leu Tyr Trp Thr Lys Trp Tyr Asn
                165                 170                 175

Asn Gln Ser Leu Gly Ser Ser His Ser Phe Ile Tyr Tyr Glu Asn
        180                 185                 190

Leu Leu Leu Gly Val Pro Arg Leu Arg Gln Leu Arg Val Arg Asn Asp
            195                 200                 205

Ser Cys Val Val His Glu Asp Phe Arg Glu Asp Ile Leu Asn Cys Tyr
    210                 215                 220

Asp Val Tyr Ser Pro Asp Lys Glu Asp Gln Leu Pro Phe Gly Pro Leu
225                 230                 235                 240

Asn Gly Thr Ala Trp Thr Tyr His Ser Gln Asn Glu Leu Gly Gly Ser
                245                 250                 255

Ser His Trp Gly Arg Leu Thr Ser Tyr Ser Gly Gly Tyr Tyr Leu
            260                 265                 270

Asp Leu Pro Gly Ser Arg Gln Ala Ser Ala Glu Ala Leu Gln Gly Leu
            275                 280                 285

Gln Glu Gly Leu Trp Leu Asp Arg Gly Thr Arg Val Val Phe Ile Asp
    290                 295                 300

Phe Ser Val Tyr Asn Ala Asn Ile Asn Leu Phe Cys Ile Leu Arg Leu
305                 310                 315                 320

Val Val Glu Phe Pro Ala Thr Gly Gly Ala Ile Pro Ser Trp Gln Ile
                325                 330                 335

Arg Thr Val Lys Leu Ile Arg Tyr Val Asn Asn Trp Asp Phe Phe Ile
            340                 345                 350

Val Gly Cys Glu Val Ile Phe Cys Ile Phe Ile Phe Tyr Tyr Val Val
            355                 360                 365

Glu Glu Ile Leu Glu Ile Arg Val His Arg Phe Arg Tyr Leu Ser Ser
    370                 375                 380

Val Trp Asn Ile Leu Asp Leu Val Val Ile Leu Leu Ser Ile Val Ala
385                 390                 395                 400

Val Gly Phe His Val Phe Arg Thr Leu Glu Val Asn Arg Leu Met Gly
                405                 410                 415

Glu Leu Leu Gln Gln Pro Asp Thr Tyr Pro Asp Phe Glu Phe Leu Ala
            420                 425                 430

Phe Trp Gln Thr Gln Tyr Asn Asn Met Asn Ala Val Asn Leu Phe Phe
            435                 440                 445

Ala Trp Ile Lys Ile Phe Lys Tyr Ile Ser Phe Asn Lys Thr Met Thr
450                 455                 460

Gln Leu Ser Ser Thr Leu Ala Arg Cys Ala Lys Asp Ile Leu Gly Phe
465                 470                 475                 480

Ala Ile Met Phe Phe Ile Val Phe Phe Ala Tyr Ala Gln Leu Gly Tyr
                485                 490                 495

Leu Leu Phe Gly Thr Gln Val Glu Ser Phe Ser Thr Phe Val Lys Cys
            500                 505                 510

Ile Phe Thr Gln Phe Arg Ile Ile Leu Gly Asp Phe Asp Tyr Asn Ala
            515                 520                 525

Ile Asp Asn Ala Asn Arg Ile Leu Gly Pro Val Tyr Phe Ile Thr Tyr
        530                 535                 540

Val Phe Phe Val Phe Phe Val Leu Leu Asn Met Phe Leu Ala Ile Ile
545                 550                 555                 560

Asn Asp Thr Tyr Ser Glu Val Lys Glu Glu Leu Ala Gly Gln Arg Asp
                565                 570                 575
```

```
Gln Leu Gln Leu Ser Asp Leu Leu Lys Gln Ser Tyr Ser Lys Thr Leu
            580                 585                 590

Gln Arg Leu Arg Leu Arg Lys Glu Arg Val Ser Asp Val Gln Lys Val
            595                 600                 605

Leu Lys Gly Gly Glu Pro Glu Ile Gln Phe Glu Asp Phe Thr Asn Thr
610                 615                 620

Leu Arg Glu Leu Gly His Ala Glu Arg Glu Ile Ser Glu Val Ser Ala
625                 630                 635                 640

Ala Phe Thr Arg Phe Asp Arg Asp Gly Asp His Ile Leu Asp Glu Glu
            645                 650                 655

Asp Gln Ala Gln Met Arg Gln Gly Leu Glu Glu Arg Met Thr Leu
            660                 665                 670

Ser Ala Glu Thr Glu Asn Leu Gly Arg Ser Val Gly His Ser Pro Pro
            675                 680                 685

Gly Glu Leu Asp Ala Glu Ala Arg Gly Arg Ser Trp Val Ser Gly
690                 695                 700

Glu Glu Phe Asp Met Leu Thr Arg Arg Val Leu Gln Leu Gln Arg Val
705                 710                 715                 720

Leu Glu Gly Val Val Ser Gln Val Asp Ala Leu Ser Ser Lys Leu Lys
            725                 730                 735

Met Leu Glu Arg Lys Gly Glu Leu Ala Pro Ser Pro Gly Met Ala Met
            740                 745                 750

Pro Ala Val Trp Glu Asn Pro Tyr Asn Pro Ser
            755                 760

<210> SEQ ID NO 7
<211> LENGTH: 760
<212> TYPE: PRT
<213> ORGANISM: Mus musculus

<400> SEQUENCE: 7

Met Asn Ser Met Glu Ser Pro Lys Asn Gln Glu Leu Gln Thr Leu Gly
1               5                   10                  15

Asn Arg Ala Trp Asp Asn Pro Ala Tyr Ser Asp Pro Pro Ser Pro Asn
            20                  25                  30

Arg Thr Leu Arg Ile Cys Thr Val Ser Ser Val Ala Leu Pro Glu Thr
        35                  40                  45

Gln Pro Lys Lys Pro Glu Val Arg Cys Gln Glu Lys Thr Gln Arg Thr
    50                  55                  60

Leu Val Ser Ser Cys Cys Leu His Ile Cys Arg Ser Ile Arg Gly Leu
65                  70                  75                  80

Trp Gly Thr Thr Leu Thr Glu Asn Thr Ala Glu Asn Arg Glu Leu Tyr
                85                  90                  95

Val Lys Thr Thr Leu Arg Glu Leu Val Val Tyr Ile Val Phe Leu Val
            100                 105                 110

Asp Val Cys Leu Leu Thr Tyr Gly Met Thr Ser Ser Ala Tyr Tyr
        115                 120                 125

Tyr Thr Lys Val Met Ser Glu Leu Phe Leu His Thr Pro Ser Asp Ser
    130                 135                 140

Gly Val Ser Phe Gln Thr Ile Ser Ser Met Ser Asp Phe Trp Asp Phe
145                 150                 155                 160

Ala Gln Gly Pro Leu Leu Asp Ser Leu Tyr Trp Thr Lys Trp Tyr Asn
                165                 170                 175

Asn Gln Ser Leu Gly Arg Gly Ser His Ser Phe Ile Tyr Tyr Glu Asn
            180                 185                 190
```

```
Leu Leu Leu Gly Ala Pro Arg Leu Arg His Val Arg Val Arg Asn Asp
            195                 200                 205

Ser Cys Val Val His Glu Asp Phe Arg Glu Asp Ile Leu Asn Cys Tyr
        210                 215                 220

Asp Val Tyr Ser Pro Asp Lys Glu Asp Gln Leu Pro Phe Gly Pro Gln
225                 230                 235                 240

Asn Gly Thr Ala Trp Thr Tyr His Ser Gln Asn Glu Leu Gly Gly Ser
                245                 250                 255

Ser His Trp Gly Arg Leu Thr Ser Tyr Ser Gly Gly Tyr Tyr Leu
            260                 265                 270

Asp Leu Pro Gly Ser Arg Gln Ala Ser Ala Glu Ala Leu Gln Gly Leu
        275                 280                 285

Gln Glu Gly Leu Trp Leu Asp Arg Gly Thr Arg Val Phe Ile Asp
290                 295                 300

Phe Ser Val Tyr Asn Ala Asn Ile Asn Leu Phe Cys Ile Leu Arg Leu
305                 310                 315                 320

Val Val Glu Phe Pro Ala Thr Gly Gly Thr Ile Pro Ser Trp Gln Ile
                325                 330                 335

Arg Thr Val Lys Leu Ile Arg Tyr Val Asn Asn Trp Asp Phe Phe Ile
            340                 345                 350

Val Gly Cys Glu Val Val Phe Cys Val Phe Ile Phe Tyr Tyr Val Val
        355                 360                 365

Glu Glu Ile Leu Glu Ile His Leu His Arg Leu Arg Tyr Leu Ser Ser
        370                 375                 380

Val Trp Asn Ile Leu Asp Leu Val Val Ile Leu Leu Ser Ile Val Ala
385                 390                 395                 400

Val Gly Phe His Ile Phe Arg Thr Leu Glu Val Asn Arg Leu Met Gly
                405                 410                 415

Lys Leu Leu Gln Gln Pro Asp Thr Tyr Ala Asp Phe Glu Phe Leu Ala
            420                 425                 430

Phe Trp Gln Thr Gln Asp Asn Asn Met Asn Ala Val Asn Leu Phe Phe
        435                 440                 445

Ala Trp Ile Lys Ile Phe Lys Tyr Ile Ser Phe Asn Lys Thr Met Thr
450                 455                 460

Gln Leu Ser Ser Thr Leu Ala Arg Cys Ala Lys Asp Ile Leu Gly Phe
465                 470                 475                 480

Ala Val Met Phe Phe Ile Val Phe Phe Ala Tyr Ala Gln Leu Gly Tyr
                485                 490                 495

Leu Leu Phe Gly Thr Gln Val Glu Asn Phe Ser Thr Phe Val Lys Cys
            500                 505                 510

Ile Phe Thr Gln Phe Arg Ile Ile Leu Gly Asp Phe Asp Tyr Asn Ala
        515                 520                 525

Ile Asp Asn Ala Asn Arg Ile Leu Gly Pro Val Tyr Phe Val Thr Tyr
        530                 535                 540

Val Phe Phe Val Phe Phe Val Leu Leu Asn Met Phe Leu Ala Ile Ile
545                 550                 555                 560

Asn Asp Thr Tyr Ser Glu Val Lys Glu Glu Leu Ala Gly Gln Lys Asp
                565                 570                 575

Gln Leu Gln Leu Ser Asp Phe Leu Lys Gln Ser Tyr Asn Lys Thr Leu
            580                 585                 590

Leu Arg Leu Arg Leu Arg Lys Glu Arg Val Ser Asp Val Gln Lys Val
        595                 600                 605
```

```
Leu Lys Gly Gly Glu Pro Ile Gln Phe Glu Asp Phe Thr Ser Thr
    610                 615                 620

Leu Arg Glu Leu Gly His Glu His Glu Ile Thr Ala Ala Phe Thr
625                 630                 635                 640

Arg Phe Asp Gln Asp Gly Asp His Ile Leu Asp Glu Glu Gln Glu
                645                 650                 655

Gln Met Arg Gln Gly Leu Glu Glu Arg Val Thr Leu Asn Ala Glu
            660                 665                 670

Ile Glu Asn Leu Gly Arg Ser Val Gly His Ser Pro Gly Glu Leu
        675                 680                 685

Gly Ala Glu Ala Ala Arg Gly Gln Ser Trp Val Ser Gly Glu Phe
    690                 695                 700

Asp Met Leu Thr Arg Arg Val Leu Gln Leu Gln Cys Val Leu Glu Gly
705                 710                 715                 720

Val Val Ser Gln Ile Asp Ala Val Gly Ser Lys Leu Lys Met Leu Glu
                725                 730                 735

Arg Lys Gly Glu Leu Ala Pro Ser Pro Gly Met Gly Glu Pro Ala Val
            740                 745                 750

Trp Glu Asn Leu Tyr Asn Pro Ser
            755                 760

<210> SEQ ID NO 8
<211> LENGTH: 805
<212> TYPE: PRT
<213> ORGANISM: Homo sapiens

<400> SEQUENCE: 8

Met Asn Ala Val Gly Ser Pro Glu Gly Gln Glu Leu Gln Lys Leu Gly
1               5                   10                  15

Ser Gly Ala Trp Asp Asn Pro Ala Tyr Ser Gly Pro Ser Pro His
            20                  25                  30

Gly Thr Leu Arg Val Cys Thr Ile Ser Ser Thr Gly Pro Leu Gln Pro
        35                  40                  45

Gln Pro Lys Lys Pro Glu Asp Glu Pro Gln Glu Thr Ala Tyr Arg Thr
    50                  55                  60

Gln Val Ser Ser Cys Cys Leu His Ile Cys Gln Gly Ile Arg Gly Leu
65                  70                  75                  80

Trp Gly Thr Thr Leu Thr Glu Asn Thr Ala Glu Asn Arg Glu Leu Tyr
                85                  90                  95

Ile Lys Thr Thr Leu Arg Glu Leu Leu Val Tyr Ile Val Phe Leu Val
            100                 105                 110

Asp Ile Cys Leu Leu Thr Tyr Gly Met Thr Ser Ser Ser Ala Tyr Tyr
        115                 120                 125

Tyr Thr Lys Val Met Ser Glu Leu Phe Leu His Thr Pro Ser Asp Thr
    130                 135                 140

Gly Val Ser Phe Gln Ala Ile Ser Ser Met Ala Asp Phe Trp Asp Phe
145                 150                 155                 160

Ala Gln Gly Pro Leu Leu Asp Ser Leu Tyr Trp Thr Lys Trp Tyr Asn
                165                 170                 175

Asn Gln Ser Leu Gly His Gly Ser His Ser Phe Ile Tyr Tyr Glu Asn
            180                 185                 190

Met Leu Leu Gly Val Pro Arg Leu Arg Gln Leu Lys Val Arg Asn Asp
        195                 200                 205

Ser Cys Val Val His Glu Asp Phe Arg Glu Asp Ile Leu Ser Cys Tyr
    210                 215                 220
```

-continued

```
Asp Val Tyr Ser Pro Asp Lys Glu Glu Gln Leu Pro Phe Gly Pro Phe
225                 230                 235                 240

Asn Gly Thr Ala Trp Thr Tyr His Ser Gln Asp Glu Leu Gly Gly Phe
            245                 250                 255

Ser His Trp Gly Arg Leu Thr Ser Tyr Ser Gly Gly Tyr Tyr Leu
                260                 265                 270

Asp Leu Pro Gly Ser Arg Gln Gly Ser Ala Glu Ala Leu Arg Ala Leu
                275                 280                 285

Gln Glu Gly Leu Trp Leu Asp Arg Gly Thr Arg Val Val Phe Ile Asp
290                 295                 300

Phe Ser Val Tyr Asn Ala Asn Ile Asn Leu Phe Cys Val Leu Arg Leu
305                 310                 315                 320

Val Val Glu Phe Pro Ala Thr Gly Gly Ala Ile Pro Ser Trp Gln Ile
                325                 330                 335

Arg Thr Val Lys Leu Ile Arg Tyr Val Ser Asn Trp Asp Phe Phe Ile
                340                 345                 350

Val Gly Cys Glu Val Ile Phe Cys Val Phe Ile Phe Tyr Tyr Val Val
                355                 360                 365

Glu Glu Ile Leu Glu Leu His Ile His Arg Leu Arg Tyr Leu Ser Ser
370                 375                 380

Ile Trp Asn Ile Leu Asp Leu Val Val Ile Leu Leu Ser Ile Val Ala
385                 390                 395                 400

Val Gly Phe His Ile Phe Arg Thr Leu Glu Val Asn Arg Leu Met Gly
                405                 410                 415

Lys Leu Leu Gln Gln Pro Asn Thr Tyr Ala Asp Phe Glu Phe Leu Ala
                420                 425                 430

Phe Trp Gln Thr Gln Tyr Asn Asn Met Asn Ala Val Asn Leu Phe Phe
                435                 440                 445

Ala Trp Ile Lys Ile Phe Lys Tyr Ile Ser Phe Asn Lys Thr Met Thr
450                 455                 460

Gln Leu Ser Ser Thr Leu Ala Arg Cys Ala Lys Asp Ile Leu Gly Phe
465                 470                 475                 480

Ala Val Met Phe Phe Ile Val Phe Phe Ala Tyr Ala Gln Leu Gly Tyr
                485                 490                 495

Leu Leu Phe Gly Thr Gln Val Glu Asn Phe Ser Thr Phe Ile Lys Cys
                500                 505                 510

Ile Phe Thr Gln Phe Arg Ile Ile Leu Gly Asp Phe Asp Tyr Asn Ala
                515                 520                 525

Ile Asp Asn Ala Asn Arg Ile Leu Gly Pro Ala Tyr Phe Val Thr Tyr
530                 535                 540

Val Phe Phe Val Phe Val Leu Leu Asn Met Phe Leu Ala Ile Ile
545                 550                 555                 560

Asn Asp Thr Tyr Ser Glu Val Lys Glu Glu Leu Ala Gly Gln Lys Asp
                565                 570                 575

Glu Leu Gln Leu Ser Asp Leu Leu Lys Gln Gly Tyr Asn Lys Thr Leu
                580                 585                 590

Leu Arg Leu Arg Leu Arg Lys Glu Arg Val Ser Asp Val Gln Lys Val
                595                 600                 605

Leu Gln Gly Gly Glu Gln Glu Ile Gln Phe Glu Asp Phe Thr Asn Thr
610                 615                 620

Leu Arg Glu Leu Gly His Ala Glu His Glu Ile Thr Glu Leu Thr Ala
625                 630                 635                 640
```

-continued

```
Thr Phe Thr Lys Phe Asp Arg Asp Gly Asn Arg Ile Leu Asp Glu Lys
            645                 650                 655

Glu Gln Glu Lys Met Arg Gln Asp Leu Glu Glu Arg Val Ala Leu
            660                 665                 670

Asn Thr Glu Ile Glu Lys Leu Gly Arg Ser Ile Val Ser Ser Pro Gln
            675                 680                 685

Gly Lys Ser Gly Pro Glu Ala Ala Arg Ala Gly Gly Trp Val Ser Gly
    690                 695                 700

Glu Glu Phe Tyr Met Leu Thr Arg Arg Val Leu Gln Leu Glu Thr Val
705                 710                 715                 720

Leu Glu Gly Val Val Ser Gln Ile Asp Ala Val Gly Ser Lys Leu Lys
                725                 730                 735

Met Leu Glu Arg Lys Gly Trp Leu Ala Pro Ser Pro Gly Val Lys Glu
                740                 745                 750

Gln Ala Ile Trp Lys His Pro Gln Pro Ala Pro Ala Val Thr Pro Asp
            755                 760                 765

Pro Trp Gly Val Gln Gly Gln Glu Ser Glu Val Pro Tyr Lys Arg
    770                 775                 780

Glu Glu Glu Ala Leu Glu Glu Arg Arg Leu Ser Arg Gly Glu Ile Pro
785                 790                 795                 800

Thr Leu Gln Arg Ser
            805
```